(12) United States Patent
Estep, III et al.

(10) Patent No.: US 10,351,850 B2
(45) Date of Patent: *Jul. 16, 2019

(54) DOUBLE-STRANDED RIBONUCLEIC ACID AS CONTROL AGAINST INSECTS

(71) Applicants: The United States of America as represented by the Secretary of the Navy, Washington, DC (US); The United States of America as represented by the Secretary of Agriculture, Washington, DC (US)

(72) Inventors: Alden S. Estep, III, Middleburg, FL (US); James J. Becnel, Gainesville, FL (US); Neil D. Sanscrainte, Gainesville, FL (US)

(73) Assignees: The United States of America as represented by the Secretary of the Navy., Washington, DC (US); The United States of America as represented by the Secretary of Agriculture., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,890

(22) Filed: Sep. 20, 2017

(65) Prior Publication Data

US 2018/0010130 A1 Jan. 11, 2018

Related U.S. Application Data

(63) Continuation of application No. 14/935,759, filed on Nov. 9, 2015, now Pat. No. 9,796,975.
(60) Provisional application No. 62/077,441, filed on Nov. 10, 2014.

(51) Int. Cl.
*C12N 15/113* (2010.01)
*A01N 25/00* (2006.01)
*A01N 63/00* (2006.01)

(52) U.S. Cl.
CPC .......... *C12N 15/113* (2013.01); *A01N 25/006* (2013.01); *A01N 63/00* (2013.01); *C12N 2310/14* (2013.01); *C12N 2330/51* (2013.01)

(58) Field of Classification Search
CPC . C12N 15/113; C12N 2310/14; A01N 25/006
See application file for complete search history.

(56) References Cited

U.S. PATENT DOCUMENTS 9,796,975 B2 * 10/2017 Estep, III ............. A01N 25/006

* cited by examiner

*Primary Examiner* — Brian Whiteman
(74) *Attorney, Agent, or Firm* — Albert M. Churilla; Ning Yang; Diane P. Tso

(57) ABSTRACT

A composition for use in formulations for controlling insect populations, including populations of mosquito and flies. The composition comprises one or more double-stranded constructs inhibitory to RNA transcription of ribosomal proteins. The invention also relates to method of using the compositions in formulations to inhibit insect populations.

10 Claims, 4 Drawing Sheets

Specification includes a Sequence Listing.

SEQUENCE LISTING

```
<160> NUMBER OF SEQ ID NOS: 231

<210> SEQ ID NO 1
<211> LENGTH: 152
<212> TYPE: DNA
<213> ORGANISM: Aedes aegypti

<400> SEQUENCE: 1
gtcctgacca acacccgtgt ccgtctgctg ctgaagaagg gccactcttg ctatcgccca     60
cgtcgtaccg gagagcgcaa gcgtaagtcg gttcgcggtt gcatcgttga ccagaacctg    120
tctgccctgg ccctgatcgt cgtcaagaag gg                                  152

<210> SEQ ID NO 2
<211> LENGTH: 38
<212> TYPE: DNA
<213> ORGANISM: Aedes aegypti

<400> SEQUENCE: 2
taatacgact cactataggg gtcctgacca acacccgt                             38

<210> SEQ ID NO 3
<211> LENGTH: 40
<212> TYPE: DNA
<213> ORGANISM: Aedes aegypti

<400> SEQUENCE: 3
taatacgact cactataggg cccttcttga cgacgatcag                           40

<210> SEQ ID NO 4
<211> LENGTH: 183
<212> TYPE: DNA
<213> ORGANISM: Aedes aegypti
```

<400> SEQUENCE: 4

```
caagagccgt aagcgacatt tccaggcccc gtcgcacatc cgcaggaagc tgatgtcggc    60
gcccctgtcc aaggaactga agcaaaagta cactgtccgg tcgatgccaa tccgcaagga   120
tgatgaagtg caggtcgtcc ggggacacta caagggcaac caggtcggta aggtggtcca   180
ggt                                                                 183
```

<210> SEQ ID NO 5
<211> LENGTH: 40
<212> TYPE: DNA
<213> ORGANISM: Aedes aegypti

<400> SEQUENCE: 5

```
taatacgact cactataggg caagagccgt aagcgacatt                          40
```

<210> SEQ ID NO 6
<211> LENGTH: 40
<212> TYPE: DNA
<213> ORGANISM: Aedes aegypti

<400> SEQUENCE: 6

```
taatacgact cactataggg acctggacca ccttaccgac                          40
```

<210> SEQ ID NO 7
<211> LENGTH: 155
<212> TYPE: DNA
<213> ORGANISM: Aedes aegypti

<400> SEQUENCE: 7

```
caagaggaag cgtgaggaac tgtccaacat cctggcccat atgcgtaagg ccgcccacaa    60
gtaagctgct gcagcattgg cttgtgcgtg agaactttac accgttcgct ctgtttgtaa   120
tttaaggatt actacatccc aaaaaccttc tgtga                              155
```

<210> SEQ ID NO 8
<211> LENGTH: 40
<212> TYPE: DNA
<213> ORGANISM: Aedes aegypti

<400> SEQUENCE: 8

```
taatacgact cactataggg caagaggaag cgtgaggaac                          40
```

<210> SEQ ID NO 9
<211> LENGTH: 41
<212> TYPE: DNA
<213> ORGANISM: Aedes aegypti

<400> SEQUENCE: 9

```
taatacgact cactataggg tcacagaagg ttttgggat g                         41
```

<210> SEQ ID NO 10
<211> LENGTH: 159
<212> TYPE: DNA
<213> ORGANISM: Aedes aegypti

<400> SEQUENCE: 10

```
agctggaccc aagggtgtga agaagtccca gaccaaggaa gctatcctgg cccgtactca    60
caagccaaag ggacaacgca ccgccaaggc cgccctgccc taccagaaga agagctacgg   120
acgcctgtgg gccaaggccg tcttcaccgg atacaagcg                          159
```

```
<210> SEQ ID NO 11
<211> LENGTH: 38
<212> TYPE: DNA
<213> ORGANISM: Aedes aegypti

<400> SEQUENCE: 11
taatacgact cactataggg agctggaccc aagggtgt                              38

<210> SEQ ID NO 12
<211> LENGTH: 40
<212> TYPE: DNA
<213> ORGANISM: Aedes aegypti

<400> SEQUENCE: 12
taatacgact cactataggg cgcttgtatc cggtgaagac                            40

<210> SEQ ID NO 13
<211> LENGTH: 163
<212> TYPE: DNA
<213> ORGANISM: Aedes aegypti

<400> SEQUENCE: 13
ccagctccag atcggaaacg ttctgccaat cggtctgatg ccggaaggta ccattgtgtg      60
caacctggag gagaagaccg gtgaccgtgg caagctggcc cgtacctcgg gtaactacgc     120
ttccgtcatt gcccacaatc cggataccaa gcgtacccgt gtc                       163

<210> SEQ ID NO 14
<211> LENGTH: 38
<212> TYPE: DNA
<213> ORGANISM: Aedes aegypti

<400> SEQUENCE: 14
taatacgact cactataggg agctggaccc aagggtgt                              38

<210> SEQ ID NO 15
<211> LENGTH: 40
<212> TYPE: DNA
<213> ORGANISM: Aedes aegypti

<400> SEQUENCE: 15
taatacgact cactataggg cgcttgtatc cggtgaagac                            40

<210> SEQ ID NO 16
<211> LENGTH: 162
<212> TYPE: DNA
<213> ORGANISM: Aedes aegypti

<400> SEQUENCE: 16
aggatgccgc ctacaagtta agtggtcatc atggtcaaca cgcccacagc gccatccgtc      60
gggacgccaa ggtgaactgg atcatcaagg ccatgcacaa gcaccgtgaa ctgcgtgacc     120
tcacctccgc tggcaagagc cgtggattgg caagggcta cc                         162

<210> SEQ ID NO 17
<211> LENGTH: 40
<212> TYPE: DNA
<213> ORGANISM: Aedes aegypti

<400> SEQUENCE: 17
taatacgact cactataggg aggatgccgc ctacaagtta                            40
```

<210> SEQ ID NO 18
<211> LENGTH: 38
<212> TYPE: DNA
<213> ORGANISM: Aedes aegypti

<400> SEQUENCE: 18
taatacgact cactataggg ggtagcccct tgcccaatc                                38

<210> SEQ ID NO 19
<211> LENGTH: 155
<212> TYPE: DNA
<213> ORGANISM: Aedes aegypti

<400> SEQUENCE: 19
ccgagagctg cttaccctcg aggagaagga cgagaagcgt ctcttccaag gtaatgctct        60
gctgcgtcgt ctggttcgta tcggagtgct agatgaatcc cgcatgaagc tcgattacgt       120
tctcggtctg aagatcgaag atttcctgga gcgcc                                  155

<210> SEQ ID NO 20
<211> LENGTH: 39
<212> TYPE: DNA
<213> ORGANISM: Aedes aegypti

<400> SEQUENCE: 20
taatacgact cactataggg ccgagagctg cttaccctc                               39

<210> SEQ ID NO 21
<211> LENGTH: 38
<212> TYPE: DNA
<213> ORGANISM: Aedes aegypti

<400> SEQUENCE: 21
taatacgact cactataggg ggcgctccag gaaatctt                                38

<210> SEQ ID NO 22
<211> LENGTH: 213
<212> TYPE: DNA
<213> ORGANISM: Aedes aegypti

<400> SEQUENCE: 22
tctctttccg gcaatcgtat ggaattgttg taacacattt cgtgcaagat gtttatgccc        60
aaagcccatc gcgtcgccat ctacgagtac ctcttcaaag agggagtcct agtggcccag       120
aaggatttct atgccccgaa gcacccggag ctggaaaaca tcccgaacct gcacgtcatc       180
aagacgatgc aatcgctgaa gtccaagaac ttc                                    213

<210> SEQ ID NO 23
<211> LENGTH: 40
<212> TYPE: DNA
<213> ORGANISM: Aedes aegypti

<400> SEQUENCE: 23
taatacgact cactataggg tctctttccg gcaatcgtat                              40

<210> SEQ ID NO 24
<211> LENGTH: 41
<212> TYPE: DNA
<213> ORGANISM: Aedes aegypti

<400> SEQUENCE: 24
taatacgact cactataggg gaagttcttg gacttcagcg a                            41

```
<210> SEQ ID NO 25
<211> LENGTH: 188
<212> TYPE: DNA
<213> ORGANISM: Aedes aegypti

<400> SEQUENCE: 25
gccggtacct acatcgacaa gaaatgcccc ttcaccggac acatcgccat ccgtggccgc    60
atcctgaccg gagtggtccg taagatgaag atgcagcgga cgattgtgat ccgtcgtgac   120
tatctgcact tcatccgcaa gtacgaccgt ttcgagaagc gccaccggaa cctgagcgtg   180
catctgtc                                                             188

<210> SEQ ID NO 26
<211> LENGTH: 40
<212> TYPE: DNA
<213> ORGANISM: Aedes aegypti

<400> SEQUENCE: 26
taatacgact cactataggg gccggtacct acatcgacaa                           40

<210> SEQ ID NO 27
<211> LENGTH: 39
<212> TYPE: DNA
<213> ORGANISM: Aedes aegypti

<400> SEQUENCE: 27
taatacgact cactataggg gacagatgca cgctcaggt                            39

<210> SEQ ID NO 28
<211> LENGTH: 169
<212> TYPE: DNA
<213> ORGANISM: Aedes aegypti

<400> SEQUENCE: 28
ctgcgtcccg aaggataagg cgatcaagaa gttcgtgatc cggaacatcg tcgaagccgc    60
tgccgttcgt gatatttcgg atgcttcctg ctacaactcc tacgttctgc ccaaacttta   120
cgcaaaattg cactactgcg tatcgtgcgc cattcactcg aaggtggtc               169

<210> SEQ ID NO 29
<211> LENGTH: 39
<212> TYPE: DNA
<213> ORGANISM: Aedes aegypti

<400> SEQUENCE: 29
taatacgact cactataggg ctgcgtcccg aaggataag                            39

<210> SEQ ID NO 30
<211> LENGTH: 40
<212> TYPE: DNA
<213> ORGANISM: Aedes aegypti

<400> SEQUENCE: 30
taatacgact cactataggg gaccaccttc gagtgaatgg                           40

<210> SEQ ID NO 31
<211> LENGTH: 157
<212> TYPE: DNA
<213> ORGANISM: Aedes aegypti
```

<400> SEQUENCE: 31
taagcccaag atcgtcaaga agcggacgaa gaagttcatc cgccatcagt ccgatcgcta        60
tgacaagctt gcccccaact ggcgtaagcc gaaaggtatt gacaaccgag tgcgccgtcg        120
cttcaagggt cagtacctga tgccaaacat cggttac                                157

<210> SEQ ID NO 32
<211> LENGTH: 41
<212> TYPE: DNA
<213> ORGANISM: Aedes aegypti

<400> SEQUENCE: 32
taatacgact cactataggg taagcccaag atcgtcaaga a                            41

<210> SEQ ID NO 33
<211> LENGTH: 41
<212> TYPE: DNA
<213> ORGANISM: Aedes aegypti

<400> SEQUENCE: 33
taatacgact cactataggg gtaaccgatg tttggcatca g                            41

<210> SEQ ID NO 34
<211> LENGTH: 203
<212> TYPE: DNA
<213> ORGANISM: Aedes aegypti

<400> SEQUENCE: 34
aatcagacat ggtgaaggca cgcaaggaac ccgtcaacgc tgtccaggtc ttcggacgca        60
agaaaaccgc caccgccgtt gcgtactgca agcgcggaaa gggtctgctg cgggtgaacg        120
gccgccctct ggaccagatc gaacccaagg ttctgcagta caagctccag gagccgctgc        180
tgctgctcgg caaggaaaag ttc                                                203

<210> SEQ ID NO 35
<211> LENGTH: 40
<212> TYPE: DNA
<213> ORGANISM: Aedes aegypti

<400> SEQUENCE: 35
taatacgact cactataggg aatcagacat ggtgaaggca                              40

<210> SEQ ID NO 36
<211> LENGTH: 39
<212> TYPE: DNA
<213> ORGANISM: Aedes aegypti

<400> SEQUENCE: 36
taatacgact cactataggg gaacttttcc ttgccgagc                               39

<210> SEQ ID NO 37
<211> LENGTH: 158
<212> TYPE: DNA
<213> ORGANISM: Aedes aegypti

<400> SEQUENCE: 37
tacttccgtt tttgcgacct gtcgtcggtg gcgttcggct ctgtctcttt tggatagtag        60
attccgtact gtgcagtgtt ctccctccga gctaaggtca agttttttgac gacttgcacg       120 gttttttcgtc attgaaaatg gctctcaaca aagctgaa                              158

```
<210> SEQ ID NO 38
<211> LENGTH: 40
<212> TYPE: DNA
<213> ORGANISM: Aedes aegypti

<400> SEQUENCE: 38
taatacgact cactataggg tacttccgtt tttgcgacct                              40

<210> SEQ ID NO 39
<211> LENGTH: 40
<212> TYPE: DNA
<213> ORGANISM: Aedes aegypti

<400> SEQUENCE: 39
taatacgact cactataggg ttcagctttg ttgagagcca                              40

<210> SEQ ID NO 40
<211> LENGTH: 156
<212> TYPE: DNA
<213> ORGANISM: Aedes aegypti

<400> SEQUENCE: 40
acgctcccgg taagggtatt tcccagtcgg cgcttccgta ccgccgttcc gtgccatcgt        60
ggctgaaact gaacgccgat gacgtgaagg agcagatcaa gaagctcggc aagaagggca      120
tgacgccctc gcagatcggt atcatcctgc gtgatt                                 156

<210> SEQ ID NO 41
<211> LENGTH: 40
<212> TYPE: DNA
<213> ORGANISM: Aedes aegypti

<400> SEQUENCE: 41
taatacgact cactataggg acgctcccgg taagggtatt                              40

<210> SEQ ID NO 42
<211> LENGTH: 40
<212> TYPE: DNA
<213> ORGANISM: Aedes aegypti

<400> SEQUENCE: 42
taatacgact cactataggg aatcacgcag gatgataccg                              40

<210> SEQ ID NO 43
<211> LENGTH: 154
<212> TYPE: DNA
<213> ORGANISM: Aedes aegypti

<400> SEQUENCE: 43
tttgacagtt cttgtttcct gcgctctctt ttcgtttgtg actgaatcga cgagaacatc       60
aaaatggtca acgtacccaa gcagcgtcgt acctactgca agaagtgcaa ggtgcaccgc      120
gtccacaagg tcacgcagta caagaagtcc aagg                                   154

<210> SEQ ID NO 44
<211> LENGTH: 42
<212> TYPE: DNA
<213> ORGANISM: Aedes aegypti

<400> SEQUENCE: 44
taatacgact cactataggg tttgacagtt cttgtttcct gc                           42
```

```
<210> SEQ ID NO 45
<211> LENGTH: 41
<212> TYPE: DNA
<213> ORGANISM: Aedes aegypti

<400> SEQUENCE: 45
taatacgact cactataggg ccttggactt cttgtactgc g                  41

<210> SEQ ID NO 46
<211> LENGTH: 178
<212> TYPE: DNA
<213> ORGANISM: Aedes aegypti

<400> SEQUENCE: 46
tgacgtcacc gatttctttt cctcacgttt tcgtagtgaa cgacagcagc gaaacttgaa   60
tcaaaatggg tcgtgttcgt acaaagaccg tcaagaaggc ctctaaggtc attattgaga  120
aatactacac ccggttgacg atggatttcc acacgaacaa gcggatcgtc gaagaagt    178

<210> SEQ ID NO 47
<211> LENGTH: 41
<212> TYPE: DNA
<213> ORGANISM: Aedes aegypti

<400> SEQUENCE: 47
taatacgact cactataggg tgacgtcacc gatttctttt c                  41

<210> SEQ ID NO 48
<211> LENGTH: 39
<212> TYPE: DNA
<213> ORGANISM: Aedes aegypti

<400> SEQUENCE: 48
taatacgact cactataggg acttcttcga cgatccgct                     39

<210> SEQ ID NO 49
<211> LENGTH: 166
<212> TYPE: DNA
<213> ORGANISM: Aedes aegypti

<400> SEQUENCE: 49 tcttttccc gcagacaccg acgtgtagaa aacgtgttaa cgtagcgagt gtctattttt   60 ccattttca gcaaaatggg tttcgtgaag gttgtaaaga acaagcagta cttcaagcgt  120
taccaagtca ggttccgccg gcgtcgtgag ggcaagaccg attact                166

<210> SEQ ID NO 50
<211> LENGTH: 39
<212> TYPE: DNA
<213> ORGANISM: Aedes aegypti

<400> SEQUENCE: 50
taatacgact cactataggg tcttttccc gcagacacc                      39

<210> SEQ ID NO 51
<211> LENGTH: 40
<212> TYPE: DNA
<213> ORGANISM: Aedes aegypti

<400> SEQUENCE: 51
taatacgact cactataggg agtaatcggt cttgccctca                    40
```

```
<210> SEQ ID NO 52
<211> LENGTH: 174
<212> TYPE: DNA
<213> ORGANISM: Aedes aegypti

<400> SEQUENCE: 52
ggagtccacc actacaacgg taacaacatc gagctgggaa ccgcttgcgg aaagtacttc      60
cgtgtgtgca ccctgtcgat caccgatgcc ggagattccg atatcatccg taccctgccg     120
gaagctcagg ctgctcagca gtaagacgtc tgattttttg ttaaggccat ggga           174

<210> SEQ ID NO 53
<211> LENGTH: 40
<212> TYPE: DNA
<213> ORGANISM: Aedes aegypti

<400> SEQUENCE: 53
taatacgact cactataggg ggagtccacc actacaacgg                            40

<210> SEQ ID NO 54
<211> LENGTH: 40
<212> TYPE: DNA
<213> ORGANISM: Aedes aegypti

<400> SEQUENCE: 54
taatacgact cactataggg tcccatggcc ttaacaaaaa                            40

<210> SEQ ID NO 55
<211> LENGTH: 191
<212> TYPE: DNA
<213> ORGANISM: Aedes aegypti

<400> SEQUENCE: 55
tccagtacaa ccgcaacttc gccaacgtgg tgcaggcctt cggacgccgc cgcggaccga      60
acgccaactc gacgtaaaac ggtcgtggca tggtggtggc ctcgagtgtg tgtgctgggc     120
acggagagtg ttggagtttg taaaagtgtt ggaatttcgc tgaatgcgat catccgcgca     180
agaaaataaa c                                                          191

<210> SEQ ID NO 56
<211> LENGTH: 40
<212> TYPE: DNA
<213> ORGANISM: Aedes aegypti

<400> SEQUENCE: 56
taatacgact cactataggg tccagtacaa ccgcaacttc                            40

<210> SEQ ID NO 57
<211> LENGTH: 40
<212> TYPE: DNA
<213> ORGANISM: Aedes aegypti

<400> SEQUENCE: 57
taatacgact cactataggg gtttattttc ttgcgcggat                            40

<210> SEQ ID NO 58
<211> LENGTH: 176
<212> TYPE: DNA
<213> ORGANISM: Aedes aegypti
```

```
<400> SEQUENCE: 58
ccggagtcca ccactacaat ggtaacaaca tcgagctggg aaccgcctgc ggaaagtact    60
tccgtgtgtg caccctgtcg atcaccgatg ccggagattc cgatatcatc cgtaccctgc   120
cggaagctca ggctgctcag cagtaagacg tctgattttt tgttaaggcc atggga       176

<210> SEQ ID NO 59
<211> LENGTH: 40
<212> TYPE: DNA
<213> ORGANISM: Aedes aegypti

<400> SEQUENCE: 59
taatacgact cactataggg ccggagtcca ccactacaat                          40

<210> SEQ ID NO 60
<211> LENGTH: 40
<212> TYPE: DNA
<213> ORGANISM: Aedes aegypti

<400> SEQUENCE: 60
taatacgact cactataggg tcccatggcc ttaacaaaaa                          40

<210> SEQ ID NO 61
<211> LENGTH: 162
<212> TYPE: DNA
<213> ORGANISM: Aedes aegypti

<400> SEQUENCE: 61
tagcagaatg ctccccgta agaacaaaac cgtaaaggaa gaggtgcagg tctcgctcgg     60
tccccaggtc cgcgagggtg agatcgtctt cggagtggct cacatctacg ccagcttcaa   120
cgacaccttc gtccatgtca cggatctgtc cggcaaggaa ac                      162

<210> SEQ ID NO 62
<211> LENGTH: 40
<212> TYPE: DNA
<213> ORGANISM: Aedes aegypti

<400> SEQUENCE: 62
taatacgact cactataggg tagcagaatg ctccccgta                           40

<210> SEQ ID NO 63
<211> LENGTH: 39
<212> TYPE: DNA
<213> ORGANISM: Aedes aegypti

<400> SEQUENCE: 63
taatacgact cactataggg gtttccttgc cggacagat                           39

<210> SEQ ID NO 64
<211> LENGTH: 185
<212> TYPE: DNA
<213> ORGANISM: Aedes aegypti

<400> SEQUENCE: 64
cgcagctctt ttccaatcta gctgtctaaa atagtggaag ccagtgcatt cccacagcgt    60
tcaaaatggt gaaggtgaaa tgctcggaac tgcggaccaa ggacaagaag gagctgacca   120
agcagctcga ggagctcaag actgagctgc tcaatctgcg tgtggctaag gtcaccggtg   180
gagct                                                               185
```

```
<210> SEQ ID NO 65
<211> LENGTH: 40
<212> TYPE: DNA
<213> ORGANISM: Aedes aegypti

<400> SEQUENCE: 65
taatacgact cactataggg cgcagctctt ttccaatcta                          40

<210> SEQ ID NO 66
<211> LENGTH: 40
<212> TYPE: DNA
<213> ORGANISM: Aedes aegypti

<400> SEQUENCE: 66
taatacgact cactataggg agctccaccg gtgaccttag                          40

<210> SEQ ID NO 67
<211> LENGTH: 155
<212> TYPE: DNA
<213> ORGANISM: Aedes aegypti

<400> SEQUENCE: 67
gaccgagcag caatctatca cccaacttgc tgtgccgtta ctctgtcacg ttttgctggc    60
ggttacgttg gcagaactga ccactgagga cgtgacgtca ctgttagctc ttttccatct   120
tggtttcacg aaacacaaga gcatattccg tatcg                              155

<210> SEQ ID NO 68
<211> LENGTH: 40
<212> TYPE: DNA
<213> ORGANISM: Aedes aegypti

<400> SEQUENCE: 68
taatacgact cactataggg gaccgagcag caatctatca                          40

<210> SEQ ID NO 69
<211> LENGTH: 42
<212> TYPE: DNA
<213> ORGANISM: Aedes aegypti

<400> SEQUENCE: 69
taatacgact cactataggg cgatacggaa tatgctcttg tg                       42

<210> SEQ ID NO 70
<211> LENGTH: 152
<212> TYPE: DNA
<213> ORGANISM: Aedes aegypti

<400> SEQUENCE: 70
ggtcggcaaa aataagggta cctccaaagg aggcaaaaaa ggatcgaaaa agaaggttgt    60
ggatccgttc acccgcaagg actggtacga tgtgaaggcc ccgaacatgt tctcgaaccg   120
gcaggtcggc aaaaccctgg taaaccgtac cc                                 152

<210> SEQ ID NO 71
<211> LENGTH: 40
<212> TYPE: DNA
<213> ORGANISM: Aedes aegypti

<400> SEQUENCE: 71
taatacgact cactataggg ggtcggcaaa aataagggta                          40
```

<210> SEQ ID NO 72
<211> LENGTH: 40
<212> TYPE: DNA
<213> ORGANISM: Aedes aegypti

<400> SEQUENCE: 72
taatacgact cactataggg gggtacggtt taccagggtt                      40

<210> SEQ ID NO 73
<211> LENGTH: 190
<212> TYPE: DNA
<213> ORGANISM: Aedes aegypti

<400> SEQUENCE: 73
gattcgccca acaagctgta caccctggtc acctacgtgc cagtgtccac attcaaggaa  60
ctgcagacgg agaacgttga atcgaccgag gattagatgc tgtaaattta cttacaacaa 120
aacactacct acccctattc agatagaata agtcggatgg ttcaacttgt tgcgttttg 180 tgagttggaa                                                      190

<210> SEQ ID NO 74
<211> LENGTH: 40
<212> TYPE: DNA
<213> ORGANISM: Aedes aegypti

<400> SEQUENCE: 74
taatacgact cactataggg gattcgccca acaagctgta                      40

<210> SEQ ID NO 75
<211> LENGTH: 40
<212> TYPE: DNA
<213> ORGANISM: Aedes aegypti

<400> SEQUENCE: 75
taatacgact cactataggg ttccaactca caaaaacgca                      40

<210> SEQ ID NO 76
<211> LENGTH: 176
<212> TYPE: DNA
<213> ORGANISM: Aedes aegypti

<400> SEQUENCE: 76
gaaggaatac caggtcatcg ggcgtaagct gccctcggag aaggatccga accctccgct  60
gttcaagatg cacatcttcg caccggacca gatcgtggcc aagtcccgct tctggtactt 120
cctgcggcag ctgcgtaagt tcaagaaggc caccggagag atcgtttcgg tcaagc     176

<210> SEQ ID NO 77
<211> LENGTH: 41
<212> TYPE: DNA
<213> ORGANISM: Aedes aegypti

<400> SEQUENCE: 77
taatacgact cactataggg gaaggaatac caggtcatcg g                    41

<210> SEQ ID NO 78
<211> LENGTH: 40
<212> TYPE: DNA
<213> ORGANISM: Aedes aegypti

<400> SEQUENCE: 78
taatacgact cactataggg gcttgaccga aacgatctct                      40

<210> SEQ ID NO 79
<211> LENGTH: 191
<212> TYPE: DNA
<213> ORGANISM: Aedes aegypti

<400> SEQUENCE: 79

```
tcttttgccg tgttttgttg ctagtggcca cacgtgtgct ccgttaaaat ccccgaaaaa    60
tcatggataa gtccgtcgtt ttggctcgcg tcgtcaaggt ccttggccgc accggttccc   120
agggtcagtg tacccaggtg aaggtggaat tcatcagcga gcagaaccgt cagatcatcc   180
gcaacgtcaa g                                                        191
```

<210> SEQ ID NO 80
<211> LENGTH: 40
<212> TYPE: DNA
<213> ORGANISM: Aedes aegypti

<400> SEQUENCE: 80

```
taatacgact cactataggg tcttttgccg tgttttgttg                          40
```

<210> SEQ ID NO 81
<211> LENGTH: 40
<212> TYPE: DNA
<213> ORGANISM: Aedes aegypti

<400> SEQUENCE: 81

```
taatacgact cactataggg cttgacgttg cggatgatct                          40
```

<210> SEQ ID NO 82
<211> LENGTH: 163
<212> TYPE: DNA
<213> ORGANISM: Aedes aegypti

<400> SEQUENCE: 82

```
gagtcaccaa gggattccag tacaagatgc gtgccgtaca tgcccatttc cccatcaact    60
gtgtcatcag cgagaacaac agcctggtgg agatccgtaa tttcctcgga gagaagcaca   120
tccgccgcgt ccggatgcag cccggagtga ccgttgtgaa ctc                      163
```

<210> SEQ ID NO 83
<211> LENGTH: 40
<212> TYPE: DNA
<213> ORGANISM: Aedes aegypti

<400> SEQUENCE: 83

```
taatacgact cactataggg gagtcaccaa gggattccag                          40
```

<210> SEQ ID NO 84
<211> LENGTH: 40
<212> TYPE: DNA
<213> ORGANISM: Aedes aegypti

<400> SEQUENCE: 84

```
taatacgact cactataggg gagttcacaa cggtcactcc                          40
```

<210> SEQ ID NO 85
<211> LENGTH: 156
<212> TYPE: DNA
<213> ORGANISM: Aedes aegypti

```
<400> SEQUENCE: 85
tggtgcgctc acaatacaat aagctatcaa aatgaccaac tcgaagggtt atcgtcgtgg      60
taccagggac atgttctccc gccccttcag gaagcacgga accatccccc tgtctaccta     120
cctgaaggtc tacaaagccg agactacgt ggacat                                156

<210> SEQ ID NO 86
<211> LENGTH: 40
<212> TYPE: DNA
<213> ORGANISM: Aedes aegypti

<400> SEQUENCE: 86
taatacgact cactataggg tggtgcgctc acaatacaat                            40

<210> SEQ ID NO 87
<211> LENGTH: 40
<212> TYPE: DNA
<213> ORGANISM: Aedes aegypti

<400> SEQUENCE: 87
taatacgact cactataggg atgtccacgt agtctccggc                            40

<210> SEQ ID NO 88
<211> LENGTH: 159
<212> TYPE: DNA
<213> ORGANISM: Aedes aegypti

<400> SEQUENCE: 88
tgaaggaacg cttcaaggtc aacggcaaga ccggcaacct cggaaacagt gtgtcgttcg      60
agcgccagaa gatgaaagtc tacgtcaact ctgacgtgca gtactccaag cgctacctga    120
aatacttgac caagaagtat ttgaagaaga acagcctgc                            159

<210> SEQ ID NO 89
<211> LENGTH: 40
<212> TYPE: DNA
<213> ORGANISM: Aedes aegypti

<400> SEQUENCE: 89
taatacgact cactataggg tgaaggaacg cttcaaggtc                            40

<210> SEQ ID NO 90
<211> LENGTH: 40
<212> TYPE: DNA
<213> ORGANISM: Aedes aegypti

<400> SEQUENCE: 90
taatacgact cactataggg gcaggctgtt cttcttcaaa                            40

<210> SEQ ID NO 91
<211> LENGTH: 165
<212> TYPE: DNA
<213> ORGANISM: Aedes aegypti

<400> SEQUENCE: 91
gggcttgctc caacaatcat ggtatgatcc ggaagtacgg tctcaacatt tgccgtcagt      60
gcttcaggga atacgccaag gatattggct tccggaagct ggattaaatt ccctcgacgt    120
tttctcttgc ggttcggttt attcatcacc tttgcccgaa aagat                     165
```

```
<210> SEQ ID NO 92
<211> LENGTH: 40
<212> TYPE: DNA
<213> ORGANISM: Aedes aegypti

<400> SEQUENCE: 92
taatacgact cactataggg gggcttgctc caacaatcat                    40

<210> SEQ ID NO 93
<211> LENGTH: 39
<212> TYPE: DNA
<213> ORGANISM: Aedes aegypti

<400> SEQUENCE: 93
taatacgact cactataggg atcttttcgg gcaaaggtg                     39

<210> SEQ ID NO 94
<211> LENGTH: 156
<212> TYPE: DNA
<213> ORGANISM: Aedes aegypti

<400> SEQUENCE: 94
cgatcgtatc ctaccccccaa catttcgagg aagcttttttc gtgttcgaaa gcttcccatg    60
tgcgctaaaa ctctccacaa gcatctgtca caaactccga aaaagtcaac gtcgcgagct    120
tcgctcgctg caatcgtcca tttctatttc actccc                              156

<210> SEQ ID NO 95
<211> LENGTH: 39
<212> TYPE: DNA
<213> ORGANISM: Aedes aegypti

<400> SEQUENCE: 95
taatacgact cactataggg cgatcgtatc ctaccccca                     39

<210> SEQ ID NO 96
<211> LENGTH: 42
<212> TYPE: DNA
<213> ORGANISM: Aedes aegypti

<400> SEQUENCE: 96
taatacgact cactataggg gggagtgaaa tagaaatgga cg                 42

<210> SEQ ID NO 97
<211> LENGTH: 211
<212> TYPE: DNA
<213> ORGANISM: Aedes aegypti

<400> SEQUENCE: 97
attggagcta cccgtgtcca ctttgtgcgc actcgcggtg gaaaccgtaa gttccgtgcc    60
ctccgtctgg atgccggaaa ctttgcctgg gcttcggaag gaaccgcccg caaggctcgt    120
atcatcgacg tcgtgtacaa tgcttcgaac aacgagttgg tccgaaccaa gaccctggtg    180
aagaatgcca tcatcgtgat tgatgccact c                                   211

<210> SEQ ID NO 98
<211> LENGTH: 39
<212> TYPE: DNA
<213> ORGANISM: Aedes aegypti

<400> SEQUENCE: 98
taatacgact cactataggg attggagcta cccgtgtcc                     39
```

```
<210> SEQ ID NO 99
<211> LENGTH: 40
<212> TYPE: DNA
<213> ORGANISM: Aedes aegypti

<400> SEQUENCE: 99
taatacgact cactataggg gagtggcatc aatcacgatg                          40

<210> SEQ ID NO 100
<211> LENGTH: 160
<212> TYPE: DNA
<213> ORGANISM: Aedes aegypti

<400> SEQUENCE: 100
acagtgaaaa agtccgccgg tgccaagacc gggtcgctga ccgatggagt ccgtcgttat    60
ttgaagcgca agcaacgtgt gcagaagaaa ttgttctccc tgaagaatgt gaagcgagtg   120
cgtgccgaaa agccgaaggt cgccattact gttgtgaaga                        160

<210> SEQ ID NO 101
<211> LENGTH: 39
<212> TYPE: DNA
<213> ORGANISM: Aedes aegypti

<400> SEQUENCE: 101
taatacgact cactataggg acagtgaaaa agtccgccg                          39

<210> SEQ ID NO 102
<211> LENGTH: 41
<212> TYPE: DNA
<213> ORGANISM: Aedes aegypti

<400> SEQUENCE: 102
taatacgact cactataggg tcttcacaac agtaatggcg a                       41

<210> SEQ ID NO 103
<211> LENGTH: 167
<212> TYPE: DNA
<213> ORGANISM: Aedes aegypti

<400> SEQUENCE: 103
gtgctctttt tcgccagcga tcggttctcg ttcggcctga catctttctt ttctgcttct    60
accacgtttt gctaaagttg tggtccgtac aaaatgtaca acgctgtgtc gaaaaaacgc   120
cggttcgttg ccaatggcat gttccgtgct gaattgaacg agttcct                167

<210> SEQ ID NO 104
<211> LENGTH: 38
<212> TYPE: DNA
<213> ORGANISM: Aedes aegypti

<400> SEQUENCE: 104
taatacgact cactataggg gtgctctttt tcgccagc                           38

<210> SEQ ID NO 105
<211> LENGTH: 41
<212> TYPE: DNA
<213> ORGANISM: Aedes aegypti

<400> SEQUENCE: 105
taatacgact cactataggg aggaactcgt tcaattcagc a                       41
```

<210> SEQ ID NO 106
<211> LENGTH: 167
<212> TYPE: DNA
<213> ORGANISM: Aedes aegypti

<400> SEQUENCE: 106

```
cacgtttcgg gcttcaagtt tactgatttg gaagaggcag taaaatttcg ccaaaatgaa    60
gatcggcctt tgcgcgttca gcggtttcaa gatctacccc gcaagtggta aaacattggt   120
caaagccgat ggcaagactt tcaccttcat caacaagaaa tgcgagc                 167
```

<210> SEQ ID NO 107
<211> LENGTH: 39
<212> TYPE: DNA
<213> ORGANISM: Aedes aegypti

<400> SEQUENCE: 107

```
taatacgact cactataggg cacgtttcgg gcttcaagt                            39
```

<210> SEQ ID NO 108
<211> LENGTH: 40
<212> TYPE: DNA
<213> ORGANISM: Aedes aegypti

<400> SEQUENCE: 108

```
taatacgact cactataggg gctcgcattt cttgttgatg                           40
```

<210> SEQ ID NO 109
<211> LENGTH: 154
<212> TYPE: DNA
<213> ORGANISM: Aedes aegypti

<400> SEQUENCE: 109

```
gccgaataag caagcggatg gagtattgaa ggaaaacaac attgacatcc ctcgttgtat    60
ttacggaaaa ttggaaatgt tatcgttgtc tctatgagtg caacgataac aggaaaatac   120
aaaacatgat ttgatgctgt gaatgtgctt tggt                                154
```

<210> SEQ ID NO 110
<211> LENGTH: 39
<212> TYPE: DNA
<213> ORGANISM: Aedes aegypti

<400> SEQUENCE: 110

```
taatacgact cactataggg gccgaataag caagcggat                            39
```

<210> SEQ ID NO 111
<211> LENGTH: 40
<212> TYPE: DNA
<213> ORGANISM: Aedes aegypti

<400> SEQUENCE: 111

```
taatacgact cactataggg accaaagcac attcacagca                           40
```

<210> SEQ ID NO 112
<211> LENGTH: 159
<212> TYPE: DNA
<213> ORGANISM: Aedes aegypti

<400> SEQUENCE: 112
ccgagtggcc aaattgatga agctgcgcgg aaaggatgag aacaccattg ccgtcgttgt         60
cggaaccgtg accaacgatg accgcaagct gtactgcccg aagatgaatg tgtgtgccct        120
gcgtgtgacg gaaaaggccc gtgagcgtat cctgaagtg                               159

<210> SEQ ID NO 113
<211> LENGTH: 38
<212> TYPE: DNA
<213> ORGANISM: Aedes aegypti

<400> SEQUENCE: 113
taatacgact cactataggg ccgagtggcc aaattgat                                 38

<210> SEQ ID NO 114
<211> LENGTH: 40
<212> TYPE: DNA
<213> ORGANISM: Aedes aegypti

<400> SEQUENCE: 114
taatacgact cactataggg cacttcagga tacgctcacg                               40

<210> SEQ ID NO 115
<211> LENGTH: 164
<212> TYPE: DNA
<213> ORGANISM: Aedes aegypti

<400> SEQUENCE: 115
gaagaatggt ccgcattagt gtgctagccg atgcgctcaa gtgcatcaac aatgccgaga         60
agcgtggaaa acgccaggtc ctgatccggc ccaacagtaa agtcgtgatc aagttcctga       120
ccgtgatgat gaagcatggc tacatcggag agttcgaaat cgtc                         164

<210> SEQ ID NO 116
<211> LENGTH: 42
<212> TYPE: DNA
<213> ORGANISM: Aedes aegypti

<400> SEQUENCE: 116
taatacgact cactataggg gaagaatggt ccgcattagt gt                            42

<210> SEQ ID NO 117
<211> LENGTH: 40
<212> TYPE: DNA
<213> ORGANISM: Aedes aegypti

<400> SEQUENCE: 117
taatacgact cactataggg gacgatttcg aactctccga                               40

<210> SEQ ID NO 118
<211> LENGTH: 188
<212> TYPE: DNA
<213> ORGANISM: Aedes aegypti

<400> SEQUENCE: 118
ctgtacgtca agaagcagcg caccgtgcca aaatgcggcc agtgcaagga gaagctgagc         60
ggaatcaagc catcccggcc gagcgagcgc ccacgtatgt gccgccgtct gaagaccgtg        120
acccgaacct tcggtggtgt cctctgccat cgttgtctcc gtgaacgcat cgtccgtgca       180
ttcctgat                                                                 188

```
<210> SEQ ID NO 119
<211> LENGTH: 40
<212> TYPE: DNA
<213> ORGANISM: Aedes aegypti

<400> SEQUENCE: 119
taatacgact cactataggg ctgtacgtca agaagcagcg                            40

<210> SEQ ID NO 120
<211> LENGTH: 38
<212> TYPE: DNA
<213> ORGANISM: Aedes aegypti

<400> SEQUENCE: 120
taatacgact cactataggg atcaggaatg cacggacg                              38

<210> SEQ ID NO 121
<211> LENGTH: 189
<212> TYPE: DNA
<213> ORGANISM: Aedes aegypti

<400> SEQUENCE: 121
cactctgacc gccgtctacg atgccatcct ggaggatctg gtcttcccgg ctgaagtcgt      60
cggcaagcgt atgcgcgtca agctggacgg atcgcagctg atcaaggtgc acctggacaa    120
gaaccagcag accaccattg aacacaaggt cgacaccttc acgtcagtgt acaagaagct    180
gaccggacg                                                            189

<210> SEQ ID NO 122
<211> LENGTH: 39
<212> TYPE: DNA
<213> ORGANISM: Aedes aegypti

<400> SEQUENCE: 122
taatacgact cactataggg cactctgacc gccgtctac                             39

<210> SEQ ID NO 123
<211> LENGTH: 40
<212> TYPE: DNA
<213> ORGANISM: Aedes aegypti

<400> SEQUENCE: 123
taatacgact cactataggg cgtccggtca gcttcttgta                            40

<210> SEQ ID NO 124
<211> LENGTH: 179
<212> TYPE: DNA
<213> ORGANISM: Aedes aegypti

<400> SEQUENCE: 124
cggtgagggt tccaagactt gggatcgctt ccagatgcgc ctgcacaagc gtatcatcga      60
tctgcactcg ccatcggaga tcgtcaagca gatcacctcg atcaacatcg aacccggtgt    120
agaggtcgag gtcaccatcg ccgacccttg agcgattcgt tcttgttgcg ttccccaat     179

<210> SEQ ID NO 125
<211> LENGTH: 39
<212> TYPE: DNA
<213> ORGANISM: Aedes aegypti

<400> SEQUENCE: 125
taatacgact cactataggg cggtgagggt tccaagact                             39
```

```
<210> SEQ ID NO 126
<211> LENGTH: 39
<212> TYPE: DNA
<213> ORGANISM: Aedes aegypti

<400> SEQUENCE: 126
taatacgact cactataggg attggggaac gcaacaaga                          39

<210> SEQ ID NO 127
<211> LENGTH: 188
<212> TYPE: DNA
<213> ORGANISM: Aedes aegypti

<400> SEQUENCE: 127
agtacaaccg caacttcgcc aacgtggtgc aggccttcgg acgccgccgc ggaccgaacg   60
ccaactcgac gtaaaacggt tgagacatgg tggtggcctc gagtgtgtgt gctgggcacg  120
gagagtgttg gagtttgtaa aagtgttgga atttcgctga atgcgatcgt ccgcgcaaga  180
aaataaac                                                          188

<210> SEQ ID NO 128
<211> LENGTH: 39
<212> TYPE: DNA
<213> ORGANISM: Aedes aegypti

<400> SEQUENCE: 128
taatacgact cactataggg agtacaaccg caacttcgc                          39

<210> SEQ ID NO 129
<211> LENGTH: 40
<212> TYPE: DNA
<213> ORGANISM: Aedes aegypti

<400> SEQUENCE: 129
taatacgact cactataggg gtttattttc ttgcgcggac                         40

<210> SEQ ID NO 130
<211> LENGTH: 155
<212> TYPE: DNA
<213> ORGANISM: Aedes aegypti

<400> SEQUENCE: 130
gagtatcgct cttttccgg catctgccag tcgattacag tagacacatt ttcgctctgc    60
tgagttaaaa ctcgttaaaa atgtcgctcg tgatcccaga gaagttccag cacattcttc  120
gtgtgctcag caccaacatc gacggtaagc gtacc                            155

<210> SEQ ID NO 131
<211> LENGTH: 41
<212> TYPE: DNA
<213> ORGANISM: Aedes aegypti

<400> SEQUENCE: 131
taatacgact cactataggg gagtatcgct cttttccgg c                        41

<210> SEQ ID NO 132
<211> LENGTH: 40
<212> TYPE: DNA
<213> ORGANISM: Aedes aegypti

<400> SEQUENCE: 132
taatacgact cactataggg ggtacgctta ccgtcgatgt                         40
```

<210> SEQ ID NO 133
<211> LENGTH: 157
<212> TYPE: DNA
<213> ORGANISM: Aedes aegypti

<400> SEQUENCE: 133
gtcattgcca agcagatcct gaatggccgc aaggtagtgg tcgtgcgctg cgaggatttg    60
cagctgtcag gacacttctt ccggaacaag ataaagttct tggcctatct gcgcaaacgg   120
tgcaatgtca atccggcccg tggcccattc catttcc                            157

<210> SEQ ID NO 134
<211> LENGTH: 40
<212> TYPE: DNA
<213> ORGANISM: Aedes aegypti

<400> SEQUENCE: 134
taatacgact cactataggg gtcattgcca agcagatcct                          40

<210> SEQ ID NO 135
<211> LENGTH: 38
<212> TYPE: DNA
<213> ORGANISM: Aedes aegypti

<400> SEQUENCE: 135
taatacgact cactataggg ggaaatggaa tgggccac                            38

<210> SEQ ID NO 136
<211> LENGTH: 160
<212> TYPE: DNA
<213> ORGANISM: Aedes aegypti

<400> SEQUENCE: 136
ccctggtgca gtccagagga cacgtcatcg atggaatttc cgagttgccc ctggtcgtct    60
ccgatgaggt ccagaagttc cagaagacca agcaggccgt cgctttcctg cgccgctcca   120
aggtctgggc cgatgtccag aaggtgtaca agtcgcagcg                         160

<210> SEQ ID NO 137
<211> LENGTH: 38
<212> TYPE: DNA
<213> ORGANISM: Aedes aegypti

<400> SEQUENCE: 137
taatacgact cactataggg ccctggtgca gtccagag                            38

<210> SEQ ID NO 138
<211> LENGTH: 40
<212> TYPE: DNA
<213> ORGANISM: Aedes aegypti

<400> SEQUENCE: 138
taatacgact cactataggg cgctgcgact tgtacacctt                          40

<210> SEQ ID NO 139
<211> LENGTH: 157
<212> TYPE: DNA
<213> ORGANISM: Aedes aegypti

```
<400> SEQUENCE: 139
ggccggtatt gaggattgtt ataccatgac gcgtggttcg accacaactc tgggtaactt      60
tgccaaggcc acctacgcgg ccattgccaa gacctacgcc ttcctgactc cggatctgtg    120
gaaggacctg ccactgagca agactccgta ccaggag                             157

<210> SEQ ID NO 140
<211> LENGTH: 40
<212> TYPE: DNA
<213> ORGANISM: Aedes aegypti

<400> SEQUENCE: 140
taatacgact cactataggg ggccggtatt gaggattgtt                            40

<210> SEQ ID NO 141
<211> LENGTH: 40
<212> TYPE: DNA
<213> ORGANISM: Aedes aegypti

<400> SEQUENCE: 141
taatacgact cactataggg ctcctggtac ggagtcttgc                            40

<210> SEQ ID NO 142
<211> LENGTH: 170
<212> TYPE: DNA
<213> ORGANISM: Aedes aegypti

<400> SEQUENCE: 142
agtcgacgga acgatggatg tcaacacagc gctgcaggaa gtgctgaaga agtccctgat     60
tgccgatgga ctggtccatg gaattcatga agcctgcaaa gctctggaca gcgtcaagc    120 tgtcctctgc atcctggccg aaagctgtga cgaaccccag tacaagaagc               170

<210> SEQ ID NO 143
<211> LENGTH: 39
<212> TYPE: DNA
<213> ORGANISM: Aedes aegypti

<400> SEQUENCE: 143
taatacgact cactataggg agtcgacgga acgatggat                             39

<210> SEQ ID NO 144
<211> LENGTH: 40
<212> TYPE: DNA
<213> ORGANISM: Aedes aegypti

<400> SEQUENCE: 144
taatacgact cactataggg gcttcttgta ctggggttcg                            40

<210> SEQ ID NO 145
<211> LENGTH: 166
<212> TYPE: DNA
<213> ORGANISM: Aedes aegypti

<400> SEQUENCE: 145
gtccggcaag ctgaaggtgc ccgactatat tgatctgatc aagaccgcca agtacaagga     60
actggccccg tccgaccagg actggttcta cgtgcgttgt gcttcgatcc tgcgtcgcct    120
gtaccaccag agcccggctg gagttggttc catctgccgg atctac                    166
```

```
<210> SEQ ID NO 146
<211> LENGTH: 38
<212> TYPE: DNA
<213> ORGANISM: Aedes aegypti

<400> SEQUENCE: 146
taatacgact cactataggg gtccggcaag ctgaaggt                        38

<210> SEQ ID NO 147
<211> LENGTH: 40
<212> TYPE: DNA
<213> ORGANISM: Aedes aegypti

<400> SEQUENCE: 147
taatacgact cactataggg gtagatccgg cagatggaac                     40

<210> SEQ ID NO 148
<211> LENGTH: 167
<212> TYPE: DNA
<213> ORGANISM: Aedes aegypti

<400> SEQUENCE: 148
cactcgttca ttacgttcgt gtacgctgaa gcaagcaaat tgtctcggct ttgttcttaa    60
atttcttccg gaagtcccta tttaacattc aagatgggta gggaggacaa agctacctgg   120
aaagccaact atttcgttaa gatcgtgcaa ctgctcgatg agtaccc                 167

<210> SEQ ID NO 149
<211> LENGTH: 41
<212> TYPE: DNA
<213> ORGANISM: Aedes aegypti

<400> SEQUENCE: 149
taatacgact cactataggg cactcgttca ttacgttcgt g                    41

<210> SEQ ID NO 150
<211> LENGTH: 40
<212> TYPE: DNA
<213> ORGANISM: Aedes aegypti

<400> SEQUENCE: 150
taatacgact cactataggg gggtactcat cgagcagttg                      40

<210> SEQ ID NO 151
<211> LENGTH: 174
<212> TYPE: DNA
<213> ORGANISM: Aedes aegypti

<400> SEQUENCE: 151
gcatatcggt ctgtgttccc gtcctgaaag agaagcgatc ccctctcgca aacttcagcg    60
caaaaccaaa cgtcaaccgg ctgccgtcgt tcgaatccgt taggttggca gcaatcatca   120
accattctct ttctttccgg tccaaaatga ccttcacacg ttttgtggag actg         174

<210> SEQ ID NO 152
<211> LENGTH: 40
<212> TYPE: DNA
<213> ORGANISM: Aedes aegypti

<400> SEQUENCE: 152
taatacgact cactataggg gcatatcggt ctgtgttccc                      40
```

```
<210> SEQ ID NO 153
<211> LENGTH: 41
<212> TYPE: DNA
<213> ORGANISM: Aedes aegypti

<400> SEQUENCE: 153
taatacgact cactataggg cagtctccac aaaacgtgtg a            41

<210> SEQ ID NO 154
<211> LENGTH: 154
<212> TYPE: DNA
<213> ORGANISM: Aedes aegypti

<400> SEQUENCE: 154
aaggccatca tcctcaagac gttcgacgat ggaacctccg ataagcagtt cggacatgct    60
ctcgttgccg gcatcgatcg ctaccccccgg cgagtgacgc gtcgcatgaa caagacccgc   120
ctgcacaagc gctccaagat aaagccgttc atca                               154

<210> SEQ ID NO 155
<211> LENGTH: 40
<212> TYPE: DNA
<213> ORGANISM: Aedes aegypti

<400> SEQUENCE: 155
taatacgact cactataggg aaggccatca tcctcaagac                          40

<210> SEQ ID NO 156
<211> LENGTH: 41
<212> TYPE: DNA
<213> ORGANISM: Aedes aegypti

<400> SEQUENCE: 156
taatacgact cactataggg tgatgaacgg ctttatcttg g                        41

<210> SEQ ID NO 157
<211> LENGTH: 154
<212> TYPE: DNA
<213> ORGANISM: Aedes aegypti

<400> SEQUENCE: 157
tgttccacat cttgtgtgag gacgtagtgt gaaatactcg cccaagtttt tggattttttt    60 cgggtcgaat tcccaattgt acaaccatgg ccgacacgac cgaagctgag ggagtcaaga   120
agaagcgcgc gttccgcaaa ttcacctacc gcgg                               154

<210> SEQ ID NO 158
<211> LENGTH: 41
<212> TYPE: DNA
<213> ORGANISM: Aedes aegypti

<400> SEQUENCE: 158
taatacgact cactataggg tgttccacat cttgtgtgag g                        41

<210> SEQ ID NO 159
<211> LENGTH: 38
<212> TYPE: DNA
<213> ORGANISM: Aedes aegypti

<400> SEQUENCE: 159
taatacgact cactataggg ccgcggtagg tgaatttg                            38
```

```
<210> SEQ ID NO 160
<211> LENGTH: 176
<212> TYPE: DNA
<213> ORGANISM: Aedes aegypti

<400> SEQUENCE: 160
gcaaggtgtt gcagttgttc cgtctgcgcc agatcaacaa cgccacgttc atcaagctga      60
acaaggccac caagaacatg ctgcgcattg ccgagccgta catcacctac ggatacccga     120
cgctgaaatc ggtccgccat ctgatctaca agcgtggatt cgtgaagcac cgacac        176

<210> SEQ ID NO 161
<211> LENGTH: 40
<212> TYPE: DNA
<213> ORGANISM: Aedes aegypti

<400> SEQUENCE: 161
taatacgact cactataggg gcaaggtgtt gcagttgttc                            40

<210> SEQ ID NO 162
<211> LENGTH: 39
<212> TYPE: DNA
<213> ORGANISM: Aedes aegypti

<400> SEQUENCE: 162
taatacgact cactataggg gtgtcggtgc ttcacgaat                             39

<210> SEQ ID NO 163
<211> LENGTH: 173
<212> TYPE: DNA
<213> ORGANISM: Aedes aegypti

<400> SEQUENCE: 163
ccacgggatg gttttcgtcc ggaacgattg caaggttttc agattctgcc gttcgaagtg      60
tcgtcgggcg ttcaacaaga agaagaaccc gagaaagatc cggtggacca aagcgtaccg     120
gaagaccaac ggcaaggaac tgaccatcga cccgtcgttc gagttcgaga agc            173

<210> SEQ ID NO 164
<211> LENGTH: 38
<212> TYPE: DNA
<213> ORGANISM: Aedes aegypti

<400> SEQUENCE: 164
taatacgact cactataggg ccacgggatg gttttcgt                              38

<210> SEQ ID NO 165
<211> LENGTH: 40
<212> TYPE: DNA
<213> ORGANISM: Aedes aegypti

<400> SEQUENCE: 165
taatacgact cactataggg gcttctcgaa ctcgaacgac                            40

<210> SEQ ID NO 166
<211> LENGTH: 168
<212> TYPE: DNA
<213> ORGANISM: Aedes aegypti
```

```
<400> SEQUENCE: 166
ggtcgtaagg gtcacgccgt cggtgacatt cccggagtcc gcttcaaggt ggtcaaggtg    60
gccaacgttt cgctgctggc cctgtacaag gagaagaagg aacgtccacg atcgtaagaa   120
ggggaagaaa acaaaaaacg gaatccgctg gtcgaacttt cggattct                168

<210> SEQ ID NO 167
<211> LENGTH: 38
<212> TYPE: DNA
<213> ORGANISM: Aedes aegypti

<400> SEQUENCE: 167
taatacgact cactataggg ggtcgtaagg gtcacgcc                             38

<210> SEQ ID NO 168
<211> LENGTH: 40
<212> TYPE: DNA
<213> ORGANISM: Aedes aegypti

<400> SEQUENCE: 168
taatacgact cactataggg agaatccgaa agttcgacca                           40

<210> SEQ ID NO 169
<211> LENGTH: 227
<212> TYPE: DNA
<213> ORGANISM: Aedes aegypti

<400> SEQUENCE: 169
tgtttcatcg aaaagttccg tcgagcacta caacagcaat ttaagagcac tacaacggta    60
cattttaatc ttagaacatt acaattgcaa attgtggagt accacaatag ctctttggca   120
gaacattctg gagttttctg gaattttgtt cattccaatt cgtagaatat tcttgaacat   180
ttcatcattg tcgtctgatt agaaatttgg ttggtgatca aaacgtc                 227

<210> SEQ ID NO 170
<211> LENGTH: 41
<212> TYPE: DNA
<213> ORGANISM: Aedes aegypti

<400> SEQUENCE: 170
taatacgact cactataggg tgtttcatcg aaaagttccg t                        41

<210> SEQ ID NO 171
<211> LENGTH: 40
<212> TYPE: DNA
<213> ORGANISM: Aedes aegypti

<400> SEQUENCE: 171
taatacgact cactataggg gacgttttga tcaccaacca                          40

<210> SEQ ID NO 172
<211> LENGTH: 166
<212> TYPE: DNA
<213> ORGANISM: Aedes aegypti

<400> SEQUENCE: 172
gccagacccc cgtgtactcg aaggcccgct acaccgtgcg ttcgttcgga atccgtcgta    60
acgaaaagat tgccgtccac tgcacggttc gtggattcaa ggcggaggaa atcctggagc   120
gtggtttgaa ggtccgggaa tacgagttga gacgcgacaa cttctc                  166
```

```
<210> SEQ ID NO 173
<211> LENGTH: 38
<212> TYPE: DNA
<213> ORGANISM: Aedes aegypti

<400> SEQUENCE: 173
taatacgact cactataggg gccagacccc cgtgtact                              38

<210> SEQ ID NO 174
<211> LENGTH: 40
<212> TYPE: DNA
<213> ORGANISM: Aedes aegypti

<400> SEQUENCE: 174
taatacgact cactataggg gagaagttgt cgcgtctcaa                            40

<210> SEQ ID NO 175
<211> LENGTH: 161
<212> TYPE: DNA
<213> ORGANISM: Aedes aegypti

<400> SEQUENCE: 175
gaatccgtgg tcgtctgaat cgattgcccg ccgccggagt tggtgacatg ttcgtcgcca     60
ccgtcaagaa gggtaaaccg gaactccgta agaaggtcat gccagcggtc gtcattcggc    120
agcgaaaacc cttccgcagg cgggatggcg ttttcctcta t                        161

<210> SEQ ID NO 176
<211> LENGTH: 40
<212> TYPE: DNA
<213> ORGANISM: Aedes aegypti

<400> SEQUENCE: 176
taatacgact cactataggg gaatccgtgg tcgtctgaat                            40

<210> SEQ ID NO 177
<211> LENGTH: 40
<212> TYPE: DNA
<213> ORGANISM: Aedes aegypti

<400> SEQUENCE: 177
taatacgact cactataggg atagaggaaa acgccatccc                            40

<210> SEQ ID NO 178
<211> LENGTH: 172
<212> TYPE: DNA
<213> ORGANISM: Aedes aegypti

<400> SEQUENCE: 178
ctccgatctg aaggaggttg tcaacaagct gctgcccgac tcgatcgcca aggacatcga     60
gaagtcgtgc cagggaatct acccgctgca cgatgtctac attcgcaagg ttaaggtcct    120
gaagaagccg cgcttcgatc tggccaatct gctggaactg cacggtgacg gt            172

<210> SEQ ID NO 179
<211> LENGTH: 40
<212> TYPE: DNA
<213> ORGANISM: Aedes aegypti

<400> SEQUENCE: 179
taatacgact cactataggg ctccgatctg aaggaggttg                            40
```

```
<210> SEQ ID NO 180
<211> LENGTH: 38
<212> TYPE: DNA
<213> ORGANISM: Aedes aegypti

<400> SEQUENCE: 180
taatacgact cactataggg accgtcaccg tgcagttc                              38

<210> SEQ ID NO 181
<211> LENGTH: 155
<212> TYPE: DNA
<213> ORGANISM: Aedes aegypti

<400> SEQUENCE: 181
cccgaagatg caggtgtgcg tcctcggaga ccagcagcac tgcgatgagg ccaaggccaa      60
cgacattccc tacatggatg ccgaagcgct gaagaagctg aacaagaaca agaagttggt    120
caagaaacta gccaagaagt acgacgcttt cctgg                                155

<210> SEQ ID NO 182
<211> LENGTH: 38
<212> TYPE: DNA
<213> ORGANISM: Aedes aegypti

<400> SEQUENCE: 182
taatacgact cactataggg cccgaagatg caggtgtg                              38

<210> SEQ ID NO 183
<211> LENGTH: 40
<212> TYPE: DNA
<213> ORGANISM: Aedes aegypti

<400> SEQUENCE: 183
taatacgact cactataggg ccaggaaagc gtcgtacttc                            40

<210> SEQ ID NO 184
<211> LENGTH: 152
<212> TYPE: DNA
<213> ORGANISM: Aedes aegypti

<400> SEQUENCE: 184 ctcttttttcc gtcatcttcg attgaagaaa ctgcacacat ttcgtgtcag cttttaaatt     60
tcaatcaaat ttagtaacat ttcgataaaa tggccaagcg caccaggaaa gtcggaatcg    120
tcggtaaata tggtacccga tatggtgcct cc                                   152

<210> SEQ ID NO 185
<211> LENGTH: 42
<212> TYPE: DNA
<213> ORGANISM: Aedes aegypti

<400> SEQUENCE: 185
taatacgact cactataggg ctcttttttcc gtcatcttcg at                        42

<210> SEQ ID NO 186
<211> LENGTH: 39
<212> TYPE: DNA
<213> ORGANISM: Aedes aegypti

<400> SEQUENCE: 186
taatacgact cactataggg ggaggcacca tatcgggta                             39
```

```
<210> SEQ ID NO 187
<211> LENGTH: 281
<212> TYPE: DNA
<213> ORGANISM: Aedes aegypti

<400> SEQUENCE: 187
gcgctgtctt tcgttctttt tccggcatct ttactagtgt cgagcacaca tcgaattttg      60
ctgcgagcta acaatgtcg aagagaggac gtggaggttc gcgggaggc aaattccgca      120 tctcgcttgg tctgccagtt ggcgccgtca tcaattgcgc tgataacacc ggtgctaaga      180
acctgtacgt gattgccgtc catggaatcc gtggtcgcct gaatcgattg cccgccgccg      240
gagttggtga catgttcgtc gccaccgtca agaagggtaa a                          281

<210> SEQ ID NO 188
<211> LENGTH: 40
<212> TYPE: DNA
<213> ORGANISM: Aedes aegypti

<400> SEQUENCE: 188
taatacgact cactataggg gcgctgtctt tcgttctttt                             40

<210> SEQ ID NO 189
<211> LENGTH: 40
<212> TYPE: DNA
<213> ORGANISM: Aedes aegypti

<400> SEQUENCE: 189
taatacgact cactataggg tttacccttc ttgacggtgg                             40

<210> SEQ ID NO 190
<211> LENGTH: 164
<212> TYPE: DNA
<213> ORGANISM: Aedes aegypti

<400> SEQUENCE: 190
cagtgcccga ttgtggagcg tttgaccaac tcgctgatga tgaagggccg caacaacggc      60
aagaagctga aggccgtccg cattgtgcgc cacgccttcg agatcatgca tctgctgacc      120
ggagaaaacc cactgcagat cgtcgtccag gccatcatca actc                       164

<210> SEQ ID NO 191
<211> LENGTH: 38
<212> TYPE: DNA
<213> ORGANISM: Aedes aegypti

<400> SEQUENCE: 191
taatacgact cactataggg cagtgcccga ttgtggag                               38

<210> SEQ ID NO 192
<211> LENGTH: 40
<212> TYPE: DNA
<213> ORGANISM: Aedes aegypti

<400> SEQUENCE: 192
taatacgact cactataggg gagttgatga tggcctggac                             40

<210> SEQ ID NO 193
<211> LENGTH: 193
<212> TYPE: DNA
<213> ORGANISM: Aedes aegypti
```

<400> SEQUENCE: 193

```
caatgaaacg tggcgagaag ttccacctgg ataactctcc ggaagcgcag gagaacttga    60
aaatgattcg gcctcggcaa atgtcctacg ttaaaaaggg ctccatagca gctttggaac   120
gaggacctaa attgggcggc caattgatgg acgttgcaat aacactacac aatctaacca   180
tcggcaaagg aac                                                      193
```

<210> SEQ ID NO 194
<211> LENGTH: 40
<212> TYPE: DNA
<213> ORGANISM: Aedes aegypti

<400> SEQUENCE: 194

```
taatacgact cactataggg caatgaaacg tggcgagaag                          40
```

<210> SEQ ID NO 195
<211> LENGTH: 40
<212> TYPE: DNA
<213> ORGANISM: Aedes aegypti

<400> SEQUENCE: 195

```
taatacgact cactataggg gttcctttgc cgatggttag                          40
```

<210> SEQ ID NO 196
<211> LENGTH: 153
<212> TYPE: DNA
<213> ORGANISM: Aedes aegypti

<400> SEQUENCE: 196

```
caaaatgtcg accgctacaa tccgtacccg ccggttcatg accaaccgtc tgctgtgccg    60
caaacagatg atctgcgatg tcctgcaccc gggtctggct tcggtcccca agaaggaaat   120
ccgtgacaag ctggccgcca tgtacaaaac cac                                153
```

<210> SEQ ID NO 197
<211> LENGTH: 40
<212> TYPE: DNA
<213> ORGANISM: Aedes aegypti

<400> SEQUENCE: 197

```
taatacgact cactataggg caaaatgtcg accgctacaa                          40
```

<210> SEQ ID NO 198
<211> LENGTH: 39
<212> TYPE: DNA
<213> ORGANISM: Aedes aegypti

<400> SEQUENCE: 198

```
taatacgact cactataggg gtggttttgt acatggcgg                           39
```

<210> SEQ ID NO 199
<211> LENGTH: 195
<212> TYPE: DNA
<213> ORGANISM: Aedes aegypti

<400> SEQUENCE: 199

```
caaagttcga ccccaatgaa attaagcacg tctacctgag atgtgtcggt ggagaagtcg    60
gcgccacttc atctttggcc cccaaaatcg gtccacttgg tctgtccccc aagaagatcg   120
gtgacgacat tgccaaggcc actggagact ggaagggtct gaagatcacc gtgtgcttga   180
ccatccagaa ccgac                                                    195
```

<210> SEQ ID NO 200
<211> LENGTH: 40
<212> TYPE: DNA
<213> ORGANISM: Aedes aegypti

<400> SEQUENCE: 200
taatacgact cactataggg caaagttcga ccccaatgaa          40

<210> SEQ ID NO 201
<211> LENGTH: 40
<212> TYPE: DNA
<213> ORGANISM: Aedes aegypti

<400> SEQUENCE: 201
taatacgact cactataggg gtcggttctg gatggtcaag          40

<210> SEQ ID NO 202
<211> LENGTH: 168
<212> TYPE: DNA
<213> ORGANISM: Aedes aegypti

<400> SEQUENCE: 202
gcgttacgtg gctgcatacc tcctggctgt cctcggcgga aacgccagcc catcgaatgc          60
cgacatcgag aagatcctga gctcggtcgg tatcgaagcg gattcgaccc gtgtcacgaa         120
agtggtcaac gagctgaagg gcaaatcggt cgaggaactg attgcctc                     168

<210> SEQ ID NO 203
<211> LENGTH: 39
<212> TYPE: DNA
<213> ORGANISM: Aedes aegypti

<400> SEQUENCE: 203
taatacgact cactataggg gcgttacgtg gctgcatac          39

<210> SEQ ID NO 204
<211> LENGTH: 40
<212> TYPE: DNA
<213> ORGANISM: Aedes aegypti

<400> SEQUENCE: 204
taatacgact cactataggg gaggcaatca gttcctcgac          40

<210> SEQ ID NO 205
<211> LENGTH: 388
<212> TYPE: DNA
<213> ORGANISM: Aedes aegypti

<400> SEQUENCE: 205
ccgataagca gttcggacat gctctcgttg ccggcatcga tcgctacccc cggcgagtga          60
cgcgtcgcat gaacaagacc cgcctgcaca agcgctccaa gataaagccg ttcatcaaga         120
tgctgaacta caaccacctg atgcccactc ggtacagcgt tccggacgtc agcctggaca         180
cgaaatattc cgccaaggac ctgaaggatc cagtcaagcg caagaaggcc cgcttccagg         240
tccgcgtcaa gttcgaggaa cgtcacaagt ccggcaagaa caagtggttc ttccagaagc         300
tgcgattcta aggagaatgt taccacttgg tttccttttt aatcgttaag aaagagtgag         360
tttctgaaga ggagggagag tgctgtgt                                           388

```
<210> SEQ ID NO 206
<211> LENGTH: 40
<212> TYPE: DNA
<213> ORGANISM: Aedes aegypti

<400> SEQUENCE: 206
taatacgact cactataggg ccgataagca gttcggacat                    40

<210> SEQ ID NO 207
<211> LENGTH: 40
<212> TYPE: DNA
<213> ORGANISM: Aedes aegypti

<400> SEQUENCE: 207
taatacgact cactataggg acacagcact ctccctcctc                    40

<210> SEQ ID NO 208
<211> LENGTH: 203
<212> TYPE: DNA
<213> ORGANISM: Aedes aegypti

<400> SEQUENCE: 208
ccgaaggatc tttcttttcg ctaaagtgcg ttcgttaaga cgtgttgagg ttttacctac    60
agtctgttaa aaaggtgca cccaaaatgt cgactgctac aatccgtacc cgccggttca    120
tgaccaaccg tctgctgtgc cgcaaacaga tgatctgcga tgtcctgcac ccgggtctgg   180
cctccgtccc caagaaggaa atc                                          203

<210> SEQ ID NO 209
<211> LENGTH: 40
<212> TYPE: DNA
<213> ORGANISM: Aedes aegypti

<400> SEQUENCE: 209
taatacgact cactataggg ccgaaggatc tttcttttcg                    40

<210> SEQ ID NO 210
<211> LENGTH: 39
<212> TYPE: DNA
<213> ORGANISM: Aedes aegypti

<400> SEQUENCE: 210
taatacgact cactataggg gatttccttc ttggggacg                     39

<210> SEQ ID NO 211
<211> LENGTH: 151
<212> TYPE: DNA
<213> ORGANISM: Aedes aegypti

<400> SEQUENCE: 211
atgcgggcgt catagtaaac aacaagggcg aaatgaaggg ttcggctatc actggccctg    60
ttgcgaagga atgtgctgat ctgtggcccc gtatcgcgtc caatgctgga tcgatagctt   120
aagagacgga ttggattgga taaggaagcg t                                 151

<210> SEQ ID NO 212
<211> LENGTH: 40
<212> TYPE: DNA
<213> ORGANISM: Aedes aegypti

<400> SEQUENCE: 212
taatacgact cactataggg atgcgggcgt catagtaaac                    40
```

<210> SEQ ID NO 213
<211> LENGTH: 40
<212> TYPE: DNA
<213> ORGANISM: Aedes aegypti

<400> SEQUENCE: 213
taatacgact cactataggg acgcttcctt atccaatcca           40

<210> SEQ ID NO 214
<211> LENGTH: 40
<212> TYPE: DNA
<213> ORGANISM: Aedes aegypti

<400> SEQUENCE: 214
taatacgact cactataggg gtgtttcgaa tccgtgtgaa           40

<210> SEQ ID NO 215
<211> LENGTH: 39
<212> TYPE: DNA
<213> ORGANISM: Aedes aegypti

<400> SEQUENCE: 215
taatacgact cactataggg acctggcttt gcattcctt            39

<210> SEQ ID NO 216
<211> LENGTH: 20
<212> TYPE: DNA
<213> ORGANISM: Aedes aegypti

<400> SEQUENCE: 216
ctcggcgagt gtatggaaat                                 20

<210> SEQ ID NO 217
<211> LENGTH: 20
<212> TYPE: DNA
<213> ORGANISM: Aedes aegypti

<400> SEQUENCE: 217
cgtagaagtg acgcagcttg                                 20

<210> SEQ ID NO 218
<211> LENGTH: 20
<212> TYPE: DNA
<213> ORGANISM: Aedes aegypti

<400> SEQUENCE: 218
ccctctttcc ttccgacatc                                 20

<210> SEQ ID NO 219
<211> LENGTH: 19
<212> TYPE: DNA
<213> ORGANISM: Aedes aegypti

<400> SEQUENCE: 219
ggcgagacga ggaaacatt                                  19

<210> SEQ ID NO 220
<211> LENGTH: 20
<212> TYPE: DNA
<213> ORGANISM: Aedes aegypti

<400> SEQUENCE: 220
gaggcagtaa aatttcgcca                                 20

```
<210> SEQ ID NO 221
<211> LENGTH: 20
<212> TYPE: DNA
<213> ORGANISM: Aedes aegypti

<400> SEQUENCE: 221
aggtgaaagt cttgccatcg                                           20

<210> SEQ ID NO 222
<211> LENGTH: 40
<212> TYPE: DNA
<213> ORGANISM: Musca domestica

<400> SEQUENCE: 222
taatacgact cactataggg tgaaacaggg tgtccttagc                     40

<210> SEQ ID NO 223
<211> LENGTH: 40
<212> TYPE: DNA
<213> ORGANISM: Musca domestica

<400> SEQUENCE: 223
taatacgact cactataggg cccttcttga cgatgaccaa                     40

<210> SEQ ID NO 224
<211> LENGTH: 40
<212> TYPE: DNA
<213> ORGANISM: Musca domestica

<400> SEQUENCE: 224
taatacgact cactataggg aaagaaccgc aagcgccatt                     40

<210> SEQ ID NO 225
<211> LENGTH: 40
<212> TYPE: DNA
<213> ORGANISM: Musca domestica

<400> SEQUENCE: 225
taatacgact cactataggg gcttggacaa ccttgccaac                     40

<210> SEQ ID NO 226
<211> LENGTH: 21
<212> TYPE: DNA
<213> ORGANISM: Musca domestica

<400> SEQUENCE: 226
ggtgttcctc caaatcagac a                                         21

<210> SEQ ID NO 227
<211> LENGTH: 20
<212> TYPE: DNA
<213> ORGANISM: Musca domestica

<400> SEQUENCE: 227
acttggccca tacgcttctc                                           20

<210> SEQ ID NO 228
<211> LENGTH: 20
<212> TYPE: DNA
<213> ORGANISM: Musca domestica

<400> SEQUENCE: 228
atgccaacgg taccaacgtt                                           20
```

```
<210> SEQ ID NO 229
<211> LENGTH: 20
<212> TYPE: DNA
<213> ORGANISM: Musca domestica

<400> SEQUENCE: 229
agctttgcga tccttgtcca                                                    20

<210> SEQ ID NO 230
<211> LENGTH: 165
<212> TYPE: DNA
<213> ORGANISM: Musca domestica

<400> SEQUENCE: 230
gtgaaacagg gtgtccttag ccatggccgt gttcgtttgt tgttgaagaa gggacactcc        60
tgctaccgtc cccgccgtac tggtgaacgt aaacgtaaat cagtccgtgg ttgcatcgtt        120
gatgccaaca tgtccgtctt ggctttggtc atcgtcaaga agggc                        165

<210> SEQ ID NO 231
<211> LENGTH: 185
<212> TYPE: DNA
<213> ORGANISM: Musca domestica

<400> SEQUENCE: 231
gaaagaaccg caagcgccat ttccaggccc cctcccacat tcgtcgtcgc cttatgtcgg        60
ctcccctctc caaggagttg cgtcaaaagt acaacgttcg ctccatgccc attcgcaagg       120
atgatgaagt gcaagttgtg cgcggccact tcaagggtaa ccaagttggc aaggttgtcc       180
aagcc                                                                   185
```

DOUBLE-STRANDED RIBONUCLEIC ACID AS CONTROL AGAINST INSECTS

CROSS-REFERENCES TO RELATED APPLICATIONS

This application is a continuation application and claims the benefit of U.S. Non-Provisional application Ser. No. 14/935,759, filed 9 Nov. 2015, which claims the benefit of Provisional Application, No. 62/077,441, filed 10 Nov. 2014.

BACKGROUND OF INVENTION

Field of Invention

The inventive subject matter relates to a composition and method for the control of mosquitoes and flies using double strand ribonucleic acid.

Background Art

Although RNAi has proven useful in functional studies for the knockdown and elucidation of individual gene effects in dipterans and has become a standard technique, development as a potential means of pest control has been slow.

Effective constructs have been fed directly to pests, expressed in bacteria, and expressed in plants (Zhu et al., 2011). Constructs have been developed and tested in *Plutella xylastella* (Bautista et al., 2009) and *Helicoverpa armigera* (Mao et al., 2007; 2011) against upregulated transcripts that confer pesticide resistance to reintroduce susceptibility to traditional pesticides.

Larval life stages of insects appear to be generally more susceptible to RNAi (Huvenne & Smagghe, 2010), and RNAi-induced mortality in adult mosquitoes is difficult to reproduce although a few sporadic successes have been published (Isoe et al., 2011; Pridgeon et al., 2008). The difficulty of causing lethal phenotypes and the slow induction of critical deficits has caused others to target genes to induce susceptibility to pathogens (Campbell et al., 2008), make dipterans refractive to flavivirus infection (Aliyari et al., 2008), or produce short-term ovarian provisioning defects (Gulia-Nuss et al., 2011; Isoe et al., 2011; Sim & Denlinger, 2009).

Due to the importance of the ribosome in protein synthesis, transcripts encoding for these ribosomal proteins were examined using RNAi in several arthropod species with interesting results. In *Drosophila melanogaster*, knockdown of ribosomal protein S3a (RPS3a) resulted in inhibition of egg maturation (Reynaud et al., 1997) and knockdown of other ribosomal targets also resulted in inhibition of oviposition in adults or mortality in larvae. A novel study by Kurscheid et al (2009) in *Rhipicephalus microplus* individually knocking down three ribosomal transcripts as well as one proteasomal transcript resulted in a reduction in oviposition. Recently, this study was repeated in the Western predatory mite and also resulted in the reduction of egg laying but no change in mortality (Wu & Hoy, 2014). In a study of diapause induction, the knockdown of RPS3a in *Culex* species caused a short term reduction in the ability to provision eggs (Sim & Denlinger, 2010).

SUMMARY OF THE INVENTION

The current invention relates to one or more compositions, for inclusion into formulations for insect populations comprising double stranded RNA (dsRNA) constructs from aligned ribosomal transcripts. Examples of insects include mosquitos, such as of *Aedes aegypti* and flies, such as *Musca domestica*.

In one embodiment, the dsRNA from mosquitos comprises a 120-716 basepair (bp) construct encoding the ribosomal protein S6. In a preferred embodiment, the construct is 152 bp, but can be any length between 120 to 716 bp. Another embodiment comprises a 120-716 bp construct encoding the ribosomal protein L26, with a preferred embodiment of 162 bp. In one embodiment, the ribosomal sequences are produced by amplification using polymerase chain reaction (PCR) primers containing T7 promoter sequences, in order to enable production of dsRNA in available transcription systems. One or more of the compositions, comprising dsRNA encoding ribosomal proteins, can be included in a formulation for control of insects, such as for mosquito or fly populations.

The methods of delivery of these dsRNA molecules could be inclusion of the composition into formulations for application through spray equipment directly onto the insects. Alternatively, the compositions can be included in a natural or artificial carbohydrate containing bait or bloodmeal, by uptake from larval growth solution, or by application through spray equipment with various formulants. In one embodiment the compositions can operate over a range of concentrations, including from 5 ng/insect to 2000 ng/insect.

DETAILED DESCRIPTION OF PREFERRED EMBODIMENTS

Figure 1:
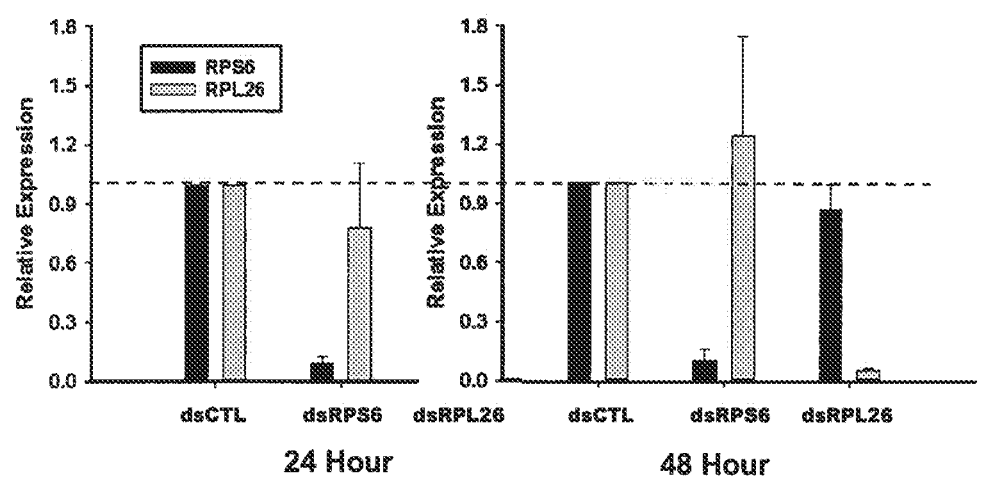
FIG. 1: Effect of double-stranded RNA at specific inhibition of target gene expression. dsRPS6 and dsRPL26 result in specific knockdown in AAG-2 cells.

Two major difficulties have limited practical development of RNAi-based pesticides for vector species; first, the necessity to develop a method to effectively deliver constructs in natural environments, and second, the development of constructs that consistently result in major alterations to the life history trajectory of the species, which could result in reduced disease. The inventive compositions address the prior art limitations by targeting transcripts of ribosomal protein S6 (RPS6) and ribosomal protein L26 (RPL26). The doubled-stranded RNA molecule, as used herein, is comprised of a sense strand, which is directly translated into protein, and a negative, complementary strand.

Example 1: Production of dsRNA

Three dsRNA constructs were manufactured and used for this study. Consensus transcript sequences for the small ribosomal subunit, RPS6, (AAEL000032), the large ribosomal subunit, RPL26, (AAEL005817) and as a control, Israeli Acute Paralysis Virus (dsIAPV) was used.

Constructs were manufactured following the instructions in the MEGASCRIPT® kit (Invitrogen™, Thermo Fischer Scientific Corporation, Waltham, Mass.) with a few modifications. Initial template was produced by PCR using *Aedes aegypti* Orlando female cDNA and T7-appended gene specific primers (Table 1). After gel purification of the initial product and sequencing to verify the expected amplicon, this was used for further template amplification to produce sufficient quantity to allow input of 1 ug of template per 20 ul MEGASCRIPT® reaction. This amplified product was concentrated and buffer exchanged twice with nuclease free water in a spin concentrator (Amicon® 30K MW MWCO, Millipore®, Billerica, Mass.) to remove impurities left from the PCR reactions. The standard MEGASCRIPT® protocol was changed to allow the use of an entire kit of 20 reactions at one time using an input of 20 ug of the appropriate T7 template. The reaction was run for 24 hours at 37 C and then purified according to the protocol. Yields from this procedure using well were between 1.5-2.0 mg of each of the three constructs. Constructs were concentrated to 20 mg/ml using Amicon® 30K MWCO concentrators and then the concentrated dsRNA was frozen. This procedure was performed 3 separate times for dsRPS6 and dsRPL26 and twice for dsHP. A 480 bp dsRNA targeting a portion of the Israeli Acute Paralysis Virus (dsIAPV) (Maori et al., 2009), which is absent from mosquitoes was used as an additional control.

Samples of dsRNA for injection were diluted in MEGASCRIPT® elution buffer to a final concentration of 10 ug/ul with 0.003% Rhodamine B dye to visualize the injected solution. A preliminary series of injections with this concentration of dye was done to ensure that no toxicity or inhibition of oviposition would result.

the two test constructs was made at 100 ug/ml in culture medium to 75-80% confluent AAG-2 cells. A previously characterized dsRNA targeting the inhibitor of apoptosis 1 transcript (dsIAPI) (AAEL009047) with known lethal activity against the AAG-2 cell line (Pridgeon et al., 2011; Liu & Clem, 2011) was used as a positive control at the same concentration. Samples were collected at 24 and 48 hours after application, washed with PBS (Gibco) and then frozen at −80 C or immediately used for RNA preparation.

In one embodiment, double-stranded RNA is utilized to knockdown ribosomal transcripts of insects, such as mosquitos. In this embodiment, double-stranded RNA from 120 to 716 base pair region of ribosomal RNA from mosquitos can be utilized. Although this example utilizes *Aedes aegypti*, any homologous ribosomal region, derived from other species, are contemplated.

In one embodiment, double-stranded RNA constructs are transcribed from nucleic acid sequences encoding ribosomal protein targets, RPS6 (AAEL000032) or RPL26 (AAEL005817), which are members of the small and large subunits, respectively. The sequences of the nucleic acid sequences whereby the double-stranded RNA are transcribed are given in SEQ ID No. 1 (RPS6) and SEQ ID No. 4 (RPL26). However, double-stranded RNA derived from other ribosomal proteins from other mosquito species can also be used. RNA can be transcribed from other nucleic acid sequences, from other mosquito ribosomal proteins, as in SEQ ID Nos. 7, 10, 13, 16, 19, 22, 25, 28, 31, 34, 37, 40, 43, 46, 49, 52, 55, 58, 61, 64, 67, 70, 73, 76, 79, 82, 85, 88,

TABLE 1

Primers for *Aedes aegypti* dsRNA construction and qPCR analysis

| Name | Sequence | Amplicon Size[1] | SEQ No. |
|---|---|---|---|
| T7F-AAEL000032RB | taatacgactcactatagggGTCCTGACCAACACCCGT | | 2 |
| T7R-AAEL000032RB | taatacgactcactatagggCCCTTCTTGACGACGATCAG | 192 | 3 |
| T7F-AAEL005817 | taatacgactcactatagggCAAGAGCCGTAAGCGACATT | | 5 |
| T7R-AAEL005817 | taatacgactcactatagggACCTGGACCACCTTACCGAC | 223 | 6 |
| T7F-AEEL009056 | taatacgactcactatagggGTGTTTCGAATCCGTGTGAA | | 220 |
| T7R-AAEL009056 | taatacgactcactatagggACCTGGCTTTGCATTCCTT | 253 | 221 |
| qRpS6_F | CTCGGCGAGTGTATGGAAAT | | 214 |
| qRpS6_R | CGTAGAAGTGACGCAGCTTG | 116 | 215 |
| qRpL26_F | CCCTCTTTCCTTCCGACATC | | 216 |
| qRpL26_R | GGCGAGACGAGGAAACATT | 105 | 217 |
| qIAPV F | GAGGCAGTAAAATTTCGCCA | | 218 |
| qIAPV R | AGGTGAAAGTCTTGCCATCG | 113 | 219 |

[1]amplicon size of templates for dsRNA includes 40 bases contributed by the T7 promoters of the fusion primers that are not present in the final dsRNA product.

Example 2: Knockdown of Ribosomal Transcripts of *Aedes aegypti*

Analysis of the constructs in Table 1 was conducted using AAG-2 cells. AAG-2 cells were grown in Eagle's media (GIBCO) supplemented with 15% FBS (Lonza Inc., Ga.) in a 5% CO2 environment at 27 C. Cells were passaged weekly in T75 flasks with 10 ml of culture media. For experimental purposes, 200,000 cells were plated into each well of a 24-well flat-bottom tissue culture plate (BD, USA) after dissociation from the previous flask approximately 24 hours before use. Two replicate plates were made for collection and processing after 24 and 48 hours of exposure to dsRNA. Application of the two control dsRNA constructs as well as 91, 94, 97, 100, 103, 106, 109, 112, 115, 118, 121, 124, 127, 130, 133, 136, 139, 142, 146, 149, 152, 155, 158, 161, 164, 167, 170, 173, 176, 179, 182, 185, 188, 191, 194, 197, 200, 203, 206, 209, and 212.

In order to evaluate the effectiveness of the double-stranded RNA sequences at inhibiting transcription of ribosomal proteins expression of the large and small ribosomal RNA was quantitatively measured in the presence of the RNA. As a control, dsIAPV double-stranded RNA was synthesized using primers encoded by SEQ ID Nos. 220 (fwd) and 221 (rev). Quantitation of the expression of RPS 6, RPL26 and IAPV was evaluated using quantitative PCR using the primers encoded by SEQ ID Nos. 214-219 (Table 1).

We performed an initial analysis in the *Ae. aegypti* AAG-2 cell line to examine the specificity of our dsRNA triggers and ensure we were reducing transcript levels of the expected targets.

As illustrated in FIG. 1, AAG-2 cells treated with 100 ug/ml of dsRNA trigger showed transcript specific reductions in gene expression after 24 and 48 hours of exposure. cDNA prepared from treated cells were examined for relative expression of either RPS6 or RPL126. Results indicate that each dsRNA specifically reduced target expression but not the expression of the other two targets. As primer efficiencies ranged between 1.94 and 1.98, expression values were calculated using the ΔΔCt method of Livak & Schmittgen (2001). Amplification conditions and amplicons are as described in the methods. This data represents two replicate experiments. Error bars represent mean±SD.

We observed no change in morphology in the cells treated with the controls (dsGFP or dsMOSQ), dsRPS6 or dsRPL26 after 24 or 48 hours of exposure. We did see the expected morphological changes in the dsIAPI treated cells (Pridgeon et al., 2011) within 24 hours and cell death by 48 h indicating that the system was functional. Samples were collected and analyzed for gene expression levels of RPS6, and RPL26 (FIG. 1). At 24 and 48 hours there was significant knockdown of RPS6 and RPL26 levels in cells treated with dsRPS6 or dsRPL26, respectively. No significant knockdown of RPS6 or RPL26 expression was observed in dsIAPV treated cells. We also did not observe significant knockdown of RPS6 expression in dsRPL26 treated cells or RPL26 knockdown in dsRPS6 treated cells indicating low crosstalk between the triggers. From this, we conclude the dsRPS6 and dsRPL26 triggers were accurately targeting the expected transcripts though we did not see visible morphological changes in the dsRPL26 of dsRPS6 treated cells.

Example 3: Evaluation of Mosquitos Following Introduction of dsRNA

In these studies, glass capillaries were pulled to a fine tip using a KOPF® (Tujunga, Calif.) Model 720 needle puller with settings at 16.8 (resistance setting) and a pull strength of 4. A needle was placed into a NANOJECT™ 2000 (World Products Inc., FL) and the tip was broken to provide a sharp point. The device was set to deliver 100 nl per injection. The needle was filled with 3-4 ul of a test solution containing either a control dsRNA (dsIAPV) or test dsRNA construct (dsRPS6 or dsRPL26). Three to five day old females were manually aspirated into a BIOQUIP® (Rancho Dominguez, Calif.) holding tube and cold anesthetized in a laboratory refrigerator at 3-4 C. Three replicate groups, of 11 mosquitoes each, were placed on the dorsal aspect on chilled slides placed into 15 cm petri dishes and aligned to allow easy injection. Plates and slides with aligned mosquitoes were maintained at 4 C until injected as we have not observed any mortality in this strain even after 24 hours of chilling. For injection, the slide with 11 mosquitoes was placed onto a BIOQUIP® Model 1614 chill table, the needle was primed and then introduced through the middle one-third of the mesokatepisternum. To visually ensure delivery of the solution, two measures were assessed during injection; the meniscus in the needle had to move upon injection and the pink color of the Rhodamine B must be visible through the cuticle at the ventral junction of the thorax and abdomen. If either of these measures were not seen, the mosquito was removed from the group. Successive injections followed the same procedure. Groups of approximately 10 mosquitoes were allowed to recover in an inverted screened cup (TK35™) (SOLO® (Dart Container Corporation, Road Mason, Mich.)) placed over sucrose saturated cotton. This recovery method, adapted from Isoe et al. (2011), resulted in less than 5% initial mortality in injected mosquitoes.

Oviposition Assays

An experimental timeline for these experiments is shown in Table 2. Cohorts of injected mosquitoes were allowed to recover for three days post-injection (PI) and then provided access to a warmed blood meal for 15 minutes or until all mosquitoes in the cup were visibly fed. Mosquitoes that did not feed were given an immediate second attempt with another warmed blood meal. If a mosquito did not feed after the second try, it was removed from the experiment. Blooded females were returned to 10% sucrose and maintained under standard temperature and humidity conditions. Two to three days post-blood meal (PBM) (6 d PI) the females were gently aspirated into individual oviposition cups (TK35™) (SOLO®) that contained 60 ml of deionized water and a 3 cm by 4 cm strip of soaked seed germination paper (Anchor Paper Co., Saint Paul, Minn.) for deposition of eggs. Oviposition cups were provided with 10% sucrose saturated cotton. Oviposition and mortality were tracked daily and eggs were counted after an additional 4 days at 10 d PI. Females were aspirated to new oviposition cups and given a second blood meal 2 days after transfer (12 d PI). Some individual mosquitoes from each group were collected and frozen for further analysis at 13 d PI. The same collection procedure was repeated after the second blood meal and eggs were counted at 20 d PI. Females were frozen for qPCR analysis after this second oviposition cycle in five of the six experiments.

TABLE 2

Experimental timeline and sample collection timepoints

| Day Post-Emergence | Action |
|---|---|
| 3 | Cold anesthetize and inject dsRNA |
| 6 | Provide first bloodmeal |
| 8 | Split into individual oviposition cups |
| 12 | Collect eggs from first oviposition cycle |
| 13 | Collect organisms for qPCR |
| 14 | Provide second bloodmeal |
| 20 | Collect eggs from second cycle |
| 21 | Collect organisms for qPCR |
| 23 | Provide third bloodmeal |
| 29 | Collect eggs from third cycle[1] |
|  | Collect remaining organisms for qPCR[1] |
| 30+ | Rear embryonated eggs to examine viability |

[1] A third oviposition cycle was only tracked in the first of the six experiments. Due to increasing mortality in all samples after 20 days post-injection, this third cycle was abandoned.

In the first experiment, the mosquitoes were taken through the oviposition procedure for a third cycle rather than frozen. Some samples were collected at 29 d PI for analysis but the majority of mosquitoes in all groups had died so this was not repeated in future experiments.

Sample Preparation

*Aedes aegypti* (Orlando strain) were in continuous colony. They were collected near Orlando, Fla. in 1952. The Center for Medical, Agricultural and Veterinary Entomology CMAVE (Gainesville, Fla.) *Aedes aegypti* rearing protocol is highly standardized and has been described previously (Pridgeon et al., 2007; Clark et al., 2011). Initially, three one-hundredths of a milliliter of eggs are placed into 100 ml of deionized water along with about 50 mg of finely ground alfalfa/pig chow mixture. This container is placed under vacuum to deoxygenate for 2-4 hours and synchronize the hatch. The neonates are placed into a tray containing 3 liters of deionized water with 0.5 g of brewers yeast:liver powder (3:2). Trays are maintained at 27 C in an insectary under a 14:10 L:D cycle. Trays are fed 1 gram of 3:2 food on the following day and then again 2 days later. Pupae are collected into a 6 oz plastic cup and placed into a screened colony cage with 10% sucrose soaked cotton balls ad libitum. Under these conditions, early larval instars are completed daily, the $4^{th}$ instar requires 2 days, and pupal development takes two days. Mosquitoes emerge at the end of the seventh day after hatching and females weigh 2.5±0.3 mg (AVG±SD) each. Colonies were provided manually-defibrinated bovine blood as the protein source for colony maintenance. Mosquitoes were used for injection experiments 3-5 days after emergence and before taking a blood-meal.

Mosquitoes for analysis were immediately frozen, transferred to microcentrifuge tubes and maintained frozen at −80° C. RNA isolation was performed using a room temperature column-based RNA isolation kit (Zymo Research Corporation (Irvine, Calif.)). RNA from individual mosquitoes was purified and subjected to a DNAse digestion following the manufacturer's instructions. RNA was eluted and checked for concentration on a NANODROP™ 2000 (Thermo Fisher Scientific (Waltham, Mass.)). The $A_{260}/A_{280}$ ratio was consistently greater than 1.95. RNA was stored at −80° C. To normalize the cDNA creation step, 300 ng of input RNA was used from each sample for first strand cDNA synthesis using the AMV-RT kit (Invitrogen™), Thermo Fisher, Scientific (Waltham, Mass.) and oligo dT primers according to the manufacturer's instructions. After cDNA creation, samples were frozen at −20° C.

Quantitative PCR Analysis

Individual mosquitoes were collected after first, second, and third oviposition cycle and cDNA was prepared as above. Samples from each experiment were analyzed together on an Applied Biosystems® (Thermo Fisher Scientific (Waltham, Mass.)) STEPONE™ PLUS™ using SYBR green chemistry and the standard recipe. Specifically, the 10 ul reaction was 5.0 ul of SYBR® Select (INVITROGEN™) (Thermo Fisher Scientific (Waltham, Mass.), 3.0 ul of combined 3 µM forward and reverse primers, 1.5 ul of nuclease free water, and 0.5 ul of sample cDNA. Primers for qPCR, (see Table 1, SEQ ID Nos. 214-219) were designed using the Primer3 server; the amplicon specified to be 85-125 bp, the $T_m$ optimized for 60 C, and the amplicon was required to cross an exon/exon junction. The qPCR amplicon was also directed to a region outside that targeted by the dsRNA construct to prevent any possible amplification of residual T7 template. Reactions were run in at least technical duplicates in 10 ul volume. Melt curve analysis followed qPCR to ensure that only one product was being amplified. Although initial testing determined consistent results were produced when run under FAST conditions, standard cycling conditions were used. Each 96-well plate from a particular experiment was provided with a common control sample to allow plate to plate comparison. Relative quantification was performed by comparison to an L24 control gene which has been shown to be relatively consistent over the range of samples examined (Pridgeon et al., 2009; Choi et al., 2013). Comparison between samples used the $2^{-DDct}$ method (Schmittgen & Livak, 2008) and test samples were normalized to expression of samples treated with elution buffer only. Template dilution curves were performed to ensure the primer efficiencies were adequately close to allow comparison using the Livak method.

Statistical Analysis

All statistical analysis were performed in JMP® (Statistical Analysis Institute (Cary, N.C.)) and methods were varied based on the character of the data and number of samples. To examine possible significant differences in oviposition levels of mosquitoes, percentages laying were sorted by dsRNA treatment group for both blood meals in each of the six experiments and then subjected to Kruskal-Wallis nonparametric analysis after initial data characterization indicated a non-normal distribution in some samples that produced low numbers of laying mosquitoes. Means separation was performed using Sennett's test.

Analysis of clutch size data showed normal distribution indicating the acceptability for use of a parametric analysis like analysis of variance (ANOVA). To identify significant interactions, pairwise comparisons were conducted between each category.

Effect of RPS6 and RPL26 dsRNA on Ovarian Morphology

Dissections of ovaries 36 hours after ingestion of a blood meal showed morphological differences based on the trigger injected. Ovarian dissection at 36 hours after a blood meal showed differences in egg provisioning. Provisioning of eggs was proceeding as expected for dsIAPV injected mosquitoes. By comparison, developing eggs in dsRPS6 injected and dSRPL26 injected organisms were delayed or reduced. DsRPS6 appeared to produce greater inhibition of egg maturation.

Representative ovaries from dsIAPV injected mosquitoes had well developed follicles as would be expected at this stage of normal egg provisioning. The ovaries of dsRPS6 injected mosquitoes were reduced and immature although it appears that some follicles were slightly provisioned. Ovaries of dsRPL26 injected mosquitoes had some provisioning of some of the follicles but others were very immature and shrunken.

We next dissected and examined ovaries to determine if the effect observed at 36 hours PBM was also present after completion of the first oviposition cycle. The mosquitoes were 6 days PBM, at which time the controls had oviposited clutches of eggs on days 4 and 5 PBM. Dissection of ovaries again showed clear morphological differences. Remnants of the blood meal were not observed and had already been excreted from all treatments. Ovaries of control injected (dsIAPV or dsMOSQ) mosquitoes were empty or nearly empty after clutches of 48 and 63 eggs had been deposited. Dissection at six days after a blood meal (10 days post-injection), shows control dsRNA injected mosquitoes had empty or nearly empty ovaries and had laid clutches of normal size. Those injected with test dsRPS6 or dsRPL26 had laid no eggs and dissection showed only limited development in dsRPS6 treated and a mix of immature and more provisioned eggs in dsRPL26 treated.

In contrast, most mosquitoes targeted with ribosomal dsRNAs did not oviposit or laid a reduced clutch. Injection of the ribosomal dsRNA triggers resulted in immature and partially provisioned eggs. There was also a visible difference in ovary morphology between injections of dsRPL26 and dsRPS6 even though in both cases no eggs were laid. As observed at 36 hours PBM, the dsRPL26 treatment allowed more maturation than dsRPS6 treatment. Several nearly complete eggs were observed in the ovaries of the dsRPL26 treatment, however no eggs were laid during the normal oviposition period. These ovarian effects indicate that the provisioning defects induced by one introduction of these ribosomal triggers are able to persist through at least ten days.

Effects of dsRPS6 and dsRPL26 on Oviposition

We then sought to determine if dsRNA mediated knockdown of ribosomal transcripts in *Ae. aegypti* would have phenotypic effects like mortality (as in *C. elegans*) or reduced fecundity as in *Rhipicephalus microplus* (Kurscheid et al., 2009) and *Metaseiulus occidentalis* (Wu & Hoy, 2014). After dsRNA injection and subsequent blood feeding, we detected no differences in mortality between treated and control groups through 20 days of observation with less than 20% mortality in all cohorts. Mortality in all cohorts increased dramatically after day 20 but was not different between treatments. The normal laboratory lifespan of the Orlando strain is about 30 days. We did observe significant reductions in fecundity in those cohorts treated with dsRPS6 and dsRPL26 through two oviposition cycles.

Effects on Clutch Size

Figure 2:
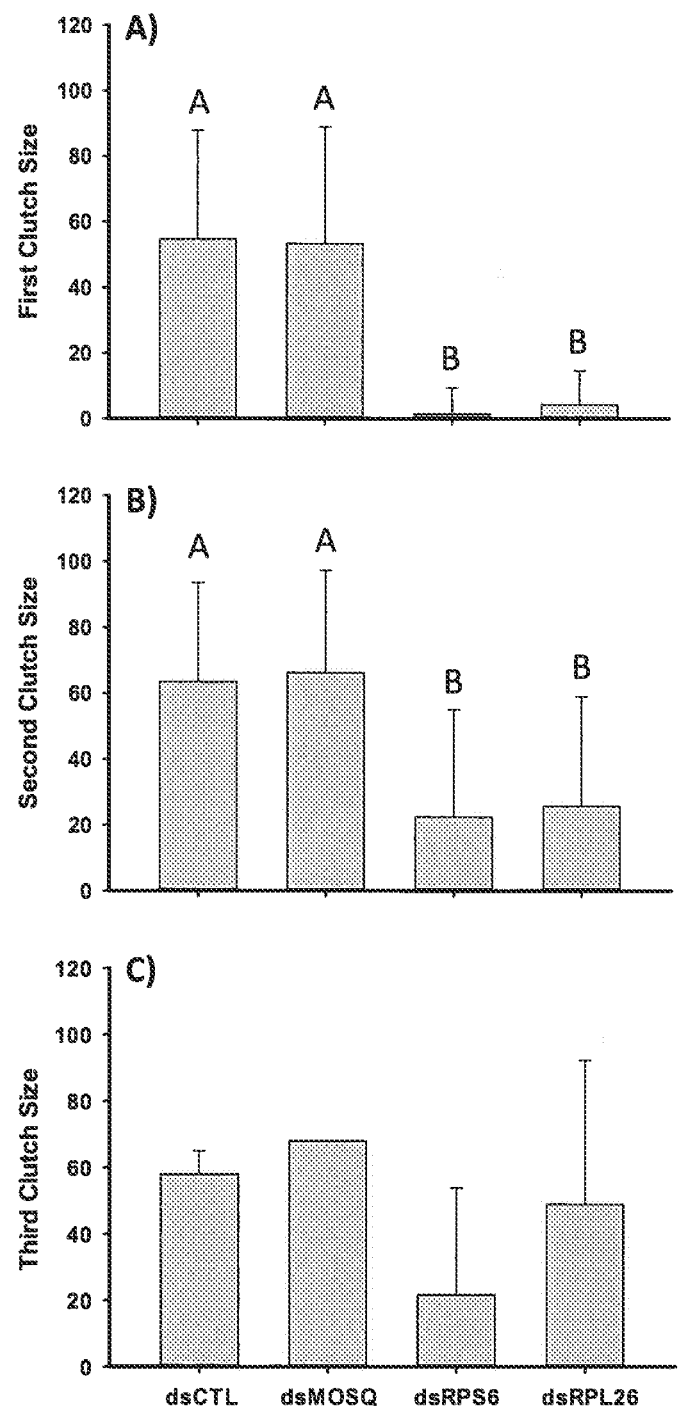
FIG. 2: Clutch size is reduced through multiple oviposition cycles in mosquitoes targeted with dsRNA against ribosomal transcripts.

We also examined whether the treatments with ribosomal specific triggers had an effect on clutch size through multiple oviposition cycles. Eggs laid by all mosquitoes from the six experiments were grouped by trigger and clutch size was plotted (FIG. 2). Eggs were counted for each organism after each oviposition cycle. Clutch size was significantly reduced after the first (A) and second (B) oviposition cycles. After the second cycle, many of the mosquitoes treated with dsRPL26 or dsRPS6 still produced no eggs or only a few eggs. Results of a third oviposition cycle (C) are shown but sample sizes were too small for statistical analysis. With the exception of (C), the data here represents combined data from six independent experiments. Significant differences are denoted by different letters over the columns. Error bars represent mean±SD.

In FIG. 2, Average clutch sizes varied significantly between the controls and test (dsRPL26 and dsRPS6) triggers (K-W test, P=<0.001, H=184.372, df=3). Average clutch sizes were calculated from the combined output of six independent experiments for the first and second oviposition cycles. An average of 54.9±33.1 (AVG±SD) eggs were produced by the dsIAPV treated and 53.3±35.7 eggs were produced by the dsMOSQ controls. The average clutches for the test dsRNA treated mosquitoes were significantly smaller at 1.2±2.3 for dsRPS6 and 43±10.4 for dsRPL26 treated mosquitoes after the first cycle (FIG. 2A). The two ribosomal dsRNAs were not significantly different from one another in pair-wise comparison. Inhibition of the total reproductive output based on these clutches was considerable; the roughly 160 mosquitoes in the control dsIAPV and dsMOSQ groups laid 8170 eggs, the 187 mosquitoes injected with the test constructs, dsRPL26 and dsRPS6 laid 471 eggs through the first cycle for a 94.2% reduction in total output. Individual samples were collected from each group in various experiments for later gene expression analysis.

Samples sizes for the second oviposition cycle are smaller based on natural death of mosquitoes, removal of those that did not take a second blood meal, and removal of live mosquitoes for dissection, RNA preparation, and gene expression analysis after the first cycle. In this case, the combined total number of mosquitoes for each construct ranged from 46-64. The results of the second cycle of blood feeding and oviposition showed a still significant (K-W test, P=<0.001, H=56.65, df=3) although a weaker effect (FIG. 2B). Control treatments (dsIAPV and dsMOSQ) both had similar mean clutch sizes of 63.5±30.1 and 66.3±31.0 eggs respectively. This was significantly different from the clutch size of dsRPS6 (22.4±32.6) and dsRPL26 (25.7±33.3) injected cohorts, which as before, were not significantly different from one another. It is interesting to note but not unexpected that the clutch size was consistently variable among the four groups and was also similar to the variability in clutch size seen in untreated *Aedes aegypti* indicating a large natural variation in fecundity. Total effect on output was again large but not of the same magnitude as observed during the first cycle. Although the sample size of the mosquitoes injected with dsRPS6 and dsRPL26 (n=96) was slightly larger than the 92 surviving control injected mosquitoes, the overall reproductive output was 2430 versus 5959, or still more than a 40% reduction.

Considering only the mosquitoes that survived through this second gonotrophic cycle, the overall effect on egg production through two cycles was impressive. The 92 control mosquitoes had a combined output from both cycles of 10848 eggs versus 2734 laid by both test groups (RPS6 and RPL26) for an overall 74.8% reduction over the life of the mosquitoes. The overall average fecundity was significantly different between the controls and test constructs (ANOVA, P<0.0001, F=72.08, df=3,197). Double stranded-RNA IAPV treated mosquitoes averaged 119.0±50.2 eggs and dsMOSQ treated averaged 116.8±57.2 for both cycles combined. Those injected with the ribosomal protein targeting triggers dsRPS6 and dsRPL26 averaged 20.8±33.6 and 31.1±37.7 eggs respectively over the two cycles. Eggs collected from both cycles of this first experiment were allowed to embryonate and then tested for viability. We observed no significant differences in the percentage of either hatching or adult emergence between eggs laid by controls or test injected cohorts.

Gene Expression in *Ae. aegypti* Orlando Strain

Figure 3:
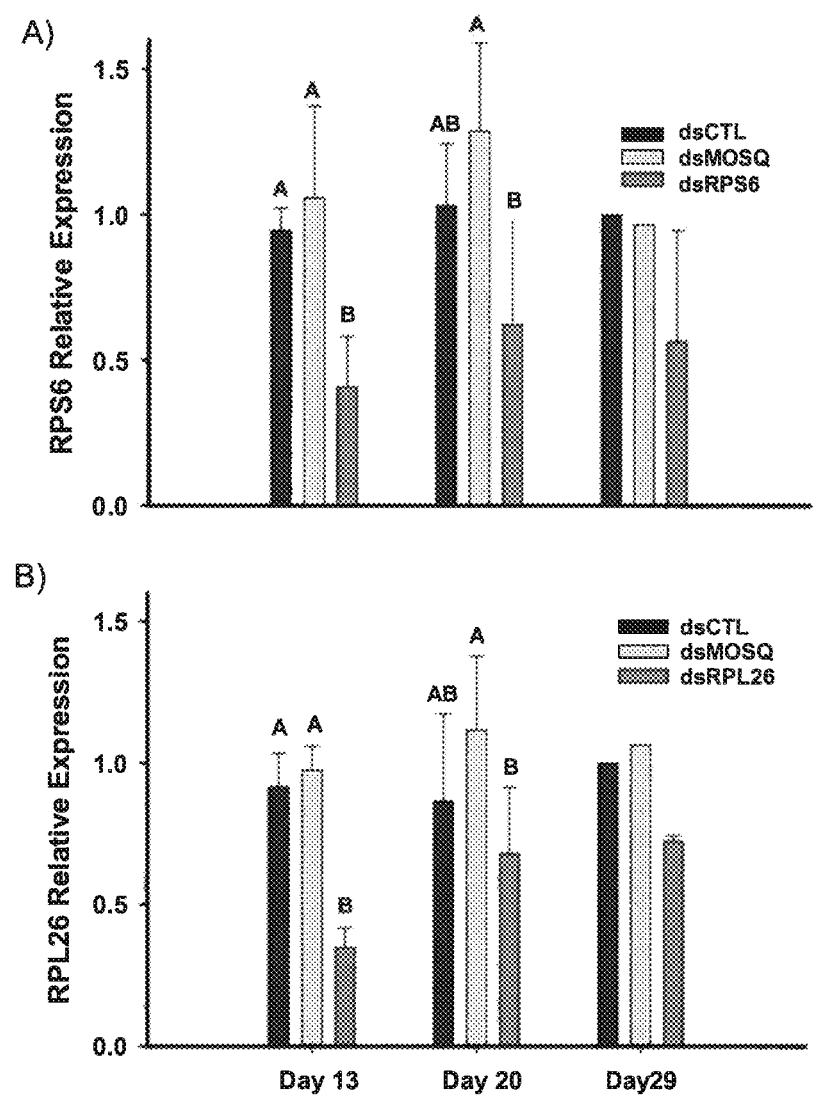
FIG. 3: The effect of dsRPS6 and dsRPL26 on gene expression is long lasting.

We examined gene expression levels of the two targeted ribosomal transcripts after treatment with dsRNA. As no effect on fecundity was observed in siRPS6 treatments, we did not include these samples in the gene expression analysis. Samples collected after the first blood meal showed a significant reduction in expression levels as compared to control dsRNA injected samples (FIG. 3). In FIG. 3, quantitative PCR analysis of samples collected after first, second and third oviposition cycles were examined for expression levels of A) RPL26 and B) RPS6. Significantly reduced expression in dsRNA-treated samples was evident after each blood meal showing a lengthy effect from a single injection of dsRNA. Calculation of RE was performed using the $2^{\wedge}ddCT$ method with the transcript level of L24 as the control gene. Efficiencies of test and control gene primer sets are from 1.94 to 1.98. Different letters represent significant differences (P<0.05) within each group. Error bars represent means±SD.

The dsIAPV and dsMOSQ injections did not result in knockdown of either the RPS6 or RPL26 transcripts. For those cohorts treated with the dsRPS6 trigger, significant knockdown was observed at both 13 and 20 days PI (FIG. 3A). Significant RPL26 knockdown was observed at d13 (FIG. 3B). By d20, some knockdown was observed but was not significant when compared to dsIAPV. However, it was significant when compared to the other control, dsMOSQ.

Effect of dsRPS6 Doses on Fecundity

Figure 4:
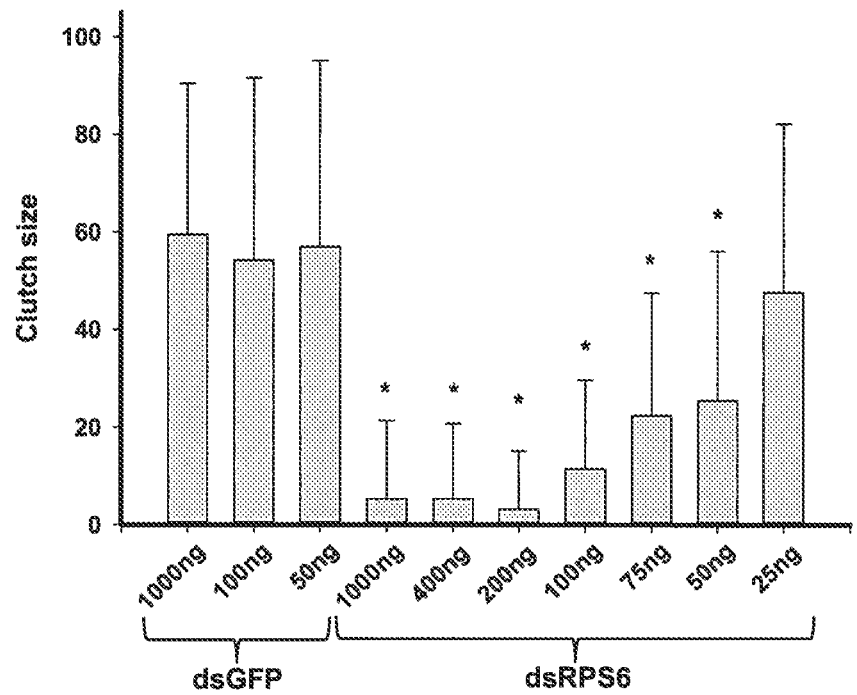
FIG. 4: Dose curve of injected dsRPS6 shows significant differences in fecundity at 50 ng/org and above.

We performed the same oviposition assay as described above over a range of lower doses of dsRPS6 than the initially tested screening dose of 1000 ng to examine the effects on oviposition (FIG. 4). In FIG. 4, injection of doses of dsRPS6 from 1000 ng/org to 50 ng/org resulted in significant reductions in fecundity in comparison to dsGFP injected cohorts (1000, 100, and 50 ng/org). Fecundity was not different than control injections at 25 ng/org of injected dsRPS6. A bloodmeal was provided three days after injection and eggs were counted on 10 days post injection. Error bars represent mean±SD from 36-81 individual organisms per dose. Columns with asterisks represent significant differences (P<0.05) from the 1000 ng/org dsGFP injected controls.

We found that injection of doses as low as 50 ng resulted in significant reductions in egg production when compared to dsGFP injected cohorts (KW test H=176.95, P<0.001, df=9). A significant difference was not observed at a dose of 25 ng. Three different doses of dsGFP also did not differ significantly. Interestingly, the mean clutch size was no different between the initial screening dose of 1000 ng and doses of 400 ng and 200 ng with an average of five eggs. At doses below 200 ng, the average clutch size began to increase.

We determined that dsRNA triggers directed against representative transcripts involved in the small or large ribosomal subunit (RPS6 or RPL26) were effective and sufficient to cause nearly complete shutdown of oviposition after blood feeding. This decrease in egg laying behavior correlates well with levels of gene expression measured from whole body preparations, and there appears to be no obvious fitness effect from knockdown of these specific ribosomal transcripts until ingestion of a blood meal. After ingestion, the organism exhibits no additional mortality even though suffering severe effects on fecundity. We also show that an siRNA trigger directed against RPS6 does not have the same effect even though it was delivered in a mass equivalent and by the same method indicating some possible selectivity in uptake. Additionally, we show one injection is long lasting (greater than 20 days), causing effects weeks afterward though a reduction of the effect occurs over time.

In contrast to other results, which also noted mortality along with fecundity decreases, no effect on general fitness was observed during these ribosomal targeting experiments. The administration of either dsRPS6 or dsRPL26 did not cause increased mortality in the adults compared to the controls. They exhibited normal behaviors; they flew, blood-fed, and excreted blood meal products even though examination by qPCR clearly showed that the specific gene targets were being affected. Even three weeks after injection, no increased mortality was observed as might be expected in an organism unable to produce the targeted ribosomes or only able to produce transcript at a reduced rate. A recent thorough study in mouse cell lines indicated that most expression regulation (>73%) is at the transcript level even though protein half-life and transcript degradation play small roles in overall phenotypic effect of gene knockdown (Jovanovic et al., 2015). It is likely the regulation effects may not be the in the same proportions in insects as it is in mammals but there is little work examining these issues in insects. Even in the quickly reproducing AAG-2 cell line, gene knockdown did not cause an increase in cell mortality as would seem to be appropriate in a tissue that was continually required to make new proteins to provision daughter cells.

A phenotypic effect that presents only after resources have been provisioned for reproduction has been observed in at least two organisms. In M. occidentalis, no mortality was noted and no gene knockdown was observed after sugar-feeding, the targeted dsRNA. However, gene knockdown was observed after the return to prey, required by this obligate predator for reproduction (Wu & Hoy, 2014) and subsequent fecundity was greatly reduced. In the mosquito, knockdown of coatomer proteins caused no mortality until the taking of a blood meal (Isoe et al., 2011). The mechanism at work behind this delayed effect is unclear. It is possible that sufficient quantities of proteins are present for day to day maintenance so transcript requirement for new synthesis would generally be low. However, taking of nutrition adequate for reproduction would require the synthesis of additional transcript to make additional proteins for provisioning of eggs. For the mite, it is proposed that an inhibitory effect results from the high sugar concentration in which the dsRNA was administered resulting in the lack of observed transcript knockdown. Our triggers were delivered by injection and therefore sucrose mediated inhibition is unlikely. Expression analysis after a blood meal of the ribosomal transcripts does not show a large spike in these levels post-blood meal as would be expected if new ribosomal transcript synthesis began (Dissanayake et al., 2010) We confirmed this with several screens of post blood-fed time point series (data not shown). An interesting possibility is that mRNAs for the ribosomal transcripts are bound in the fat body by ribonucleoprotein particles (Niu & Fallon, 2000) which may make them inaccessible to RNA induced silencing complex (RISC) cleavage. However, at this point, the mechanism behind the effect we have observed is unclear and requires further study.

We did not observe the same biological effect of reduced fecundity when siRNA targeting RPS6 was injected although dsRNA against the same target (RPS6 or RPL26) produced long-lasting effects. Both trigger formats were injected into the hemolymph but had different effects. This may indicate that the mechanism to take exogenous dsRNA into the cell from the hemolymph may have a lower size limit. Bolognesi et al. (2012) noted that dsRNA size was a critical factor in dsRNA efficacy in the western corn rootworm. It has been noted that uptake of siRNA from the gut of some insects is not as effective as dsRNA triggers (Whyard, 2015; Bolognesi et al., 2012). Intriguingly, this effect in insects is the opposite of that observed in mammals where siRNA are effective while longer dsRNA activate the interferon system leading to a general shutdown in gene expression as an antiviral response mechanism.

The use of RNAi triggering molecules as therapeutic or control agents has been advancing in mammals and plant feeding insects. In species like mosquitoes that vector human or livestock diseases, progress has been much slower. The best triggers would cause quick mortality but these have been difficult to reliably identify. Although, in the current study, significant reductions in fecundity are not as immediately effective as a traditional chemical pest control method against a vector species, the massive reductions in egg output coupled with the natural sources of mosquito mortality could quickly reduce a vector population if the construct could be effectively delivered. Future work will investigate the methods to deliver these constructs through feeding (Mang et al., 2010; Coy et al., 2012; Whyard et al., 2015) as well as work to understand specific tissue-level impacts behind the effect observed.

Example 4: Validation of RPS6 and RPL26 Targeting in the Housefly

To assess the validity of targeting species specific versions of ribosomal protein transcripts as a control method of another species, we produced a M. domestica specific constructs targeting RPS6 (SEQ ID No. 230) and RPL26 (SEQ ID No. 231). The constructs were produced in the manner described above using the primers listed in Table 3. The double-strand RNA constructs were made as for mosquitos in Example 1, using the primers SEQ ID Nos. 222-225. Quantitation of RPS6 (SEQ ID No. 226/227) and RP26 (SEQ ID No. 228/229) was by quantitative PCR using qMdom RPS6 or qMdom RPS26 primers as in Table 3. Constructs were delivered by microinjection in an initial test dose of 5 ug/female fly. Recovered flies were maintained on sucrose for three days before being given access to a protein containing food sufficient for oviposition. We clearly observed the same effect oviposition seen in mosquitoes. Dissection of gravid flies showed significant defects in ovarian provisioning in the flies that had been treated with the fly specific dsRPS6 (Mdom dsRPS6) relative to the controls. Injection of 5 ug/org of dsRPS6 resulted in significant reductions in fecundity in comparison to control organisms. Cohorts of female *M. domestica* were either not treated, injected with nuclease free water, injected with dsGFP, or injected with the described fly specific version of dsRPS6. After three days recovery, a protein source was provided to allow provisioning of eggs, ovaries were dissected and photographed. Note that the ovaries from dsRPS6 treated *M. domestica* have little to no ovarian development while controls are fully provisioned.

TABLE 3

Primers for *Musca domestica* dsRNA construction and qPCR analysis

| Name | Sequence | Amplicon Size[1] | SEQ ID No. |
| --- | --- | --- | --- |
| T7F-MdomRPS6 | taatacgactcactatagggTGAAACAGGGTGTCCTTAGC | | 222 |
| T7R-MdomRPS6 | taatacgactcactatagggCCCTTCTTGACGATGACCAA | 202 | 223 |
| T7F-MdomRPL26 | taatacgactcactatagggAAAGAACCGCAAGCGCCATT | | 224 |
| T7R-MdomRPL26 | taatacgactcactatagggGCTTGGACAACCTTGCCAAC | 222 | 225 |
| qMdomRPS6_F | GGTGTTCCTCCAAATCAGACA | | 226 |
| qMdomRPS6_R | ACTTGGCCCATACGCTTCTC | 131 | 227 |
| qMdomRPL26_F | ATGCCAACGGTACCAACGTT | | 228 |
| qMdomRPL26_R | AGCTTTGCGATCCTTGTCCA | 86 | 229 |

[1]amplicon size of templates for dsRNA includes 40 bases contributed by the T7 promoters of the fusion primers that are not present in the final dsRNA product.

Defects were not observed in those treated with control dsRNA (dsGFP) or injected with only injection buffer when compared to the ovaries of untreated flies. As in *Ae. aegypti*, this defective ovarian provisioning resulted in significant reductions in fecundity. Untreated flies produced an average of 122 eggs/female (N=51) which was similar to that of dsGFP treated cohort (136.96 eggs/female, N=53). Flies treated with *M. domestica*-specific dsRPS6 produced less than 10% of the eggs of the controls (8.14 eggs/female, N=28). This proof of concept shows that targeting RPS6 transcripts is effective in species of insect.

Example 5: Method for Control Mosquito or Fly Proteins

It is contemplated that the dsRNA can be used in a method to control insect populations, for example mosquito or fly populations. The method comprises exposing insect populations, such as breeding mosquito or fly populations, to formulations containing one or more dsRNA constructs targeting small or large ribosomal protein transcripts. The populations can be exposed to dsRNA to either the large, small or both large and small ribosomal proteins.

In order to expose the insect populations, dsRNA to insect ribosomal proteins can be included in insect bait for oral delivery of dsRNA. Alternatively, dsRNA can be incorporated into suitable insect expression systems, such as baculovirus expression systems. The expression system, incorporating nucleic acid sequences to either the small or large ribosomal proteins can then be included into insect bait or provided and exposed to insect populations via a spray or other application method.

As an example, dsRNA to the large and/or small ribosomal subunits, produced using the primers as in Table 1 or Table 3, are envisioned. Alternatively, the formulation can comprise one or more dsRNA molecules capable of inhibiting any of the ribosomal proteins. Exposure of the mosquito or fly populations to dsRNA inhibits ribosomal transcription.

The inventive method provides inhibition of oviposition in the populations, thereby reducing future populations. Clutch size is reduced through multiple oviposition cycles after an initial exposure. Maintenance of low mosquito or fly populations can be obtained by regularly treating areas with preparations containing dsRNA.

In the inventive method, the composition comprises one or more double stranded RNA molecules. The dsRNA molecules are transcribed from PCR produced ribosomal nucleic acid molecules encoding any of the ribosomal proteins. For example, the double stranded RNA molecules can be transcribed from the nucleic acid sequences selected from the group consisting of SEQ ID Nos. 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 121, 124, 127, 130, 133, 136, 139, 142, 146, 149, 152, 155, 158, 161, 164, 167, 170, 173, 176, 179, 182, 185, 188, 191, 194, 197, 200, 203, 206, 209, 212 for mosquitos or SEQ ID Nos. 230 and 231 for house flies.

In one embodiment, dsRNA encoding the small ribosomal protein, can be used to control mosquito populations, wherein the dsRNA is produced by transcription of the nucleic acid sequence of SEQ ID No. 1, produced by using the forward polymerase chain reaction primer SEQ ID No. 2 and the reverse polymerase chain reaction primer SEQ No. 3. Similarly, the large ribosomal protein can be used, wherein it is transcribed from the nucleic acid sequence of SEQ ID No. 4, produced using the forward polymerase chain reaction primer SEQ ID No. 5 and the reverse polymerase chain reaction primer SEQ ID No. 6. Production of dsRNA can be made by any method for making double stranded RNA. These compositions, alone, or together, can be incorporated into anti-insect formulations designed to control the insect populations, for example mosquito or flies.

REFERENCES

1. Aliyari, R., et al, (2008). Mechanism of Induction and Suppression of Antiviral Immunity Directed by Virus-Derived. Small RNAs in *Drosophila*. Cell host & microbe, 4(4), 387-397.
2. Amsterdam, A., et al. (2004). Identification of 315 genes essential for early zebrafish development. *Proceedings of* the *National Academy of Sciences of the United States of America,* 101(35), 12792-12797.
3. Baum, J. A., Bogaert, T., Clinton, W., Heck, G. R., Feldmann, P., Ragan, O. et al. (2007) Control of coleopteran insect pests through RNA interference. *Nature biotech* 25: 1322-1326.
4. Baum, J. A., & Roberts, J. K. (2014). Progress Towards RNAi-Mediated Insect Pest Management, *Insect Midgut and Insecticidal Proteins,* 47, 249-295.
5. Bautista, M. A. M., Miyata, T., Miura, K. and Tanaka, T. (2009) RNA interference-mediated knockdown of a cytochrome P450, CYP6BG1, from the diamondback moth, *Plutella xylostella,* reduces larval resistance to permethrin. *Insect Biochem Mol Biol* 39: 38-46.
6. Bolognesi, R., Ramaseshadri, P., Anderson, J., Bachman, P., Clinton, W., Flannagan, R., et al. (2012). Characterizing the mechanism of action of double-stranded RNA activity against western corn rootworm (*Diabrotica virgifera virgifera* LeConte). *Plos one,* 7:e47534.
7. Campbell, C. L., Keene, K. M., Brackney, D. E., Olson, K. E., Blair, C. D., Wilusz, J. et al. (2008) *Aedes aegypti* uses RNA interference in defense against Sindbis virus infection. *BMC Microbiol* 8: 47.
8. Choi, M. Y., Estep, A., Sanscrainte, N., Becnel, J., and Vander Meer, R. K. (2013) Identification and expression of PBAN/diapause hormone and GPCRs from *Aedes aegypti. Mol Cell Endocrinol* 375:113-120.
9. Clements, A. N. (2000). The Biology of Mosquitoes Volume 1: Development. *Nutrition and Reproduction* (*CABI, Wallingford, Oxfordshire, United Kingdom*), 304-408.
10. Coy, M. R., Sanscrainte, N. D., Chalaire, K. C., Inberg, A., Maayan, I., Glick, E., et al. (2012) Gene silencing in adult *Aedes aegypti* mosquitoes through oral delivery of double-stranded RNA. *J Applied Entomol* 136:741-748.
11. Cramton, S. E., and Laski, F. A. (1994) string of pearls encodes *Drosophila* ribosomal protein S2, has Minute-like characteristics, and is required during oogenesis. *Genetics,* 137(4), 1039-1048.
12. Dissanayake, S. N., Ribeiro, J. M., Wang, M. H., Dunn, W. A., Yan, G., James, A. A., & Marinotti, O. (2010) aeGEPUCI: a database of gene expression in the dengue vector mosquito, *Aedes aegypti. BMC research notes,* 3:248.
13. de la Fuente, J., Almazán, C., Naranjo, V., Blouin, E. F., Meyer, J. M., Kocan, K. M. (2006) Autocidal control of ticks by silencing of a single gene by RNA interference. *Biochem Biophys Res Comm* 344: 332-338.
14. Fire, A., Xu, S., Montgomery, M. K., Kostas, S. A., Driver, S. E., & Mello, C, C. (1998). Potent and specific genetic interference by double-stranded RNA in *Caenorhabditis elegans. Nature,* 391(6669), 806-811.
15. Garbian, Y., Maori, E., Kalev, H., Shafir, S., & Sela, I. (2012). Bidirectional transfer of RNAi between honey bee and *Varroa destructor: Varroa* gene silencing reduces *Varroa* population. *PLoS pathogens,* 8(12), e1003035.
16. Gulia-Nuss, M., Robertson, A. E., Brown, M. R., Strand, M. R. (2011) Insulin-like peptides and the target of rapamycin pathway coordinately regulate blood digestion and egg maturation in the mosquito *Aedes aegypti. PloS one* 6: e20401.
17. Hatta, T., Umemiya, R., Liao, M., Gong, H., Harnnoi, T., Tanaka, M. et al (2007) RNA interference of cytosolic leucine aminopeptidase reduces fecundity in the hard tick, *Haemaphysalis longicornis. Parasitol Res* 100: 847-854.
18. Huvenne, H. and Smagghe, G. (2010) Mechanisms of dsRNA uptake in insects and potential of RNAi for pest control: a review. *J Insect Physiol* 56: 227-235.
19. Isoe, J., Collins, J., Badgandi, H., Day, W. A. and Miesfeld, R. L. (2011) Defects in coatomer protein I (COPI) transport cause blood feeding-induced mortality in Yellow Fever mosquitoes. *Proc Nat Acad Sci* 108: E211-E217.
20. Jovanovic, M., Rooney, M. S., Mertins, P., Przybylski, D., Chevrier, N., Satija, R., and Regev, A. (2015) Dynamic profiling of the protein life cycle in response to pathogens. *Science,* 347(6226), 1259038.
21. Jin, S., Singh, N. D., Li, L., Zhang, X., Daniell, H. (2015) Engineered chloroplast dsRNA silences cytochrome P450 monooxygenase, V-ATPase and chitin synthase gene in the insect gut and disrupts *Helicoverpa armigera* larval development and pupation. *Plant Biotech J* 14:435-446.
22. Kay, M. A., and Jacobs-Lorena, M. (1987) Developmental genetics of ribosome synthesis in *Drosophila. Trends in Genetics,* 3:347-351.
23. Kim, M. J., Sim, C. Denlinger, D. L. (2010) RNA interference directed against ribosomal protein S3a suggests a link between this gene and arrested ovarian development during adult diapause in *Culex pipiens. Insect Mol Biol* 19: 27-33
24. Kocan, K. M., Manzano-Roman, R., & de la Fuente, J. (2007) Transovarial silencing of the subolesin gene in three-host ixodid tick species after injection of replete females with subolesin dsRNA. *Parasitol Res,* 100, 1411-1415.
25. Kurscheid, S., Lew-Tabor, A. E., Valle, M. R., Bruyeres, A. G., Doogan, V. J., Munderloh, U. G. et al, (2009) Evidence of a tick RNAi pathway by comparative genomics and reverse genetics screen of targets with known loss-of-function phenotypes in *Drosophila. BMC Mol Biol* 10: 26.
26. Liu, Q. and Clem, R. J. (2011) Defining the core apoptosis pathway in the mosquito disease vector *Aedes aegypti*: the roles of iap1, ark, drone, and effector caspases. *Apoptosis* 16: 105-113.
27. Livak, K. J., and Schmittgen, T. D. (2001) Analysis of relative gene expression data using real-time quantitative PCR and the 2-ΔΔCT method. *methods,* 25(4), 402-408.
28. Maeda, I., Kohara, Y., Yamamoto, M., and Sugimoto, A. (2001) Large-scale analysis of gene function in *Caenorhabditis elegans* by high-throughput RNAi. *Curr Biol* 11: 171-176.
29. Mao, Y. B., Cai, W. J., Wang, J. W., Hong, G. J., Tao, X. Y., Wang, L. et al. (2007) Silencing a cotton bollworm P450 monooxygenase gene by plant-mediated RNAi impairs larval tolerance of gossypol. *Nature Biotech* 25: 1307-1313.
30. Mao, Y. B., Tao, X. Y., Xue, X. Y., Wang, L. J. and Chen, X. Y. (2011) Cotton plants expressing CYP6AE14 double-stranded RNA show enhanced resistance to bollworms. *Transgenic Res* 20: 665-673.
31. Maori, E., Paldi, N., Shafir, S., Kalev, H., Tsur, E., Glick, E. et al (2009) IAPV, a bee-affecting virus associated with Colony Collapse Disorder can be silenced by dsRNA ingestion. *Insect Mol Biol* 18: 55-60.
32. Nishikura, K., (2001). A short primer on RNAi: RNA-directed RNA polymerase acts as a key catalyst. *Cell* 107: 415-418.
33. Niu L. L. and Fallon A. M. (2000) Differential regulation of ribosomal protein gene expression in *Aedes aegypti* mosquitoes before and after the blood meal. *Insect Mol Biol* 9: 613-623.

34. Pak, J. and Fire, A. (2007) Distinct populations of primary and secondary effectors during RNAi in *C. elegans*. *Science* 315: 241-244.
35. Perrimon, N. and Mathey-Prevot, B. (2007) Applications of high-throughput RNA interference screens to problems in cell and developmental biology. *Genetics* 175: 7-16.
36. Pridgeon, J. W., Zhao, L., Becnel, J. J., Strickman, D. A., lark, G. G., and Linthicum, K. J., (2008). Topically applied AaelAP1 double-stranded RNA kills female adults o *Aedes aegypti*. Journal of medical entomology, 45(3), 414-420.
37. Pridgeon, J. W., Becnel, J. J., Clark, G. G. and Linthicum. K. J. (2009) Permethrin induces overexpression of cytochrome c oxidase subunit 3 in *Aedes aegypti*. *J Med Entomol* 46: 810-819.
38. Pridgeon, J. W., Becnel, J. J., Strickman, D. A., (2011) U.S. Pat. No. 8,080,648B1. Washington, D.C.: U.S.
39. Raikhel, A. S. (1992) Vitellogenesis in mosquitoes. *Adv Disease Vector Res* 9:1-39.
40. Reynaud, E., Bolshakov, V. N., Barajas, V., Kafatos, F. C., & Zurita, M. (1997). Antisense suppression of the putative ribosomal protein S3A gene disrupts ovarian development in *Drosophila melanogaster*. Molecular and General Genetics MGG, 256(4), 462-467.
41. Schmittgen, T. D. and Livak, K. J. (2008) Analyzing real-time PCR data by the comparative CT method. *Nature Prot* 3: 1101-1108.
42. Sim, C. and Denlinger, D. L. (2009) A shutdown in expression of an insulin-like peptide, ILP-1, halts ovarian maturation during the overwintering diapause of the mosquito *Culex pipiens*. *Insect Mol Biol* 18: 325-332).
43. Terenius, O., Papanicolaou, A., Garbutt, J. S., Eleftherianos, l., Huvenne, H., Kanginakudru, S. et al. (2011) RNA interference in *Lepidoptera*: an overview of successful and unsuccessful studies and implications for experimental design. *J Insect Physiol* 57: 231-245.
44. Whyard, S. (2015) Insecticidal RNAi, the long and the short of it. *Science* 347: 950-951.
45. Whyard, S., Erdelyan, C. N., Partridge, A. L., Singh, A. D., Beebe, N. W., and Capina, R. (2015) Silencing the buzz: a new approach to population suppression of mosquitoes by feeding larvae double-stranded RNAs. *Parasites & vectors* 8:96.
46. Wu, K., & Hoy, M. A. (2014) Oral delivery of double-stranded RNA induces prolonged and systemic gene knockdown in *Metaseiulus occidentalis* only after feeding on *Tetranychus urticae*. *Exp App Acarol*, 63, 171-187.
47. Zhang, H., Li, H. C. and Miao, X. X. (2013) Feasibility, limitation and possible solutions of RNAi-based technology for insect pest control. *Insect Science* 20: 15-30.
48. Zhang, X., Zhang, J. and Zhu, K. Y. (2010) Chitosan/double-stranded RNA
49. nanoparticle-mediated RNA interference to silence chitin synthase genes through larval feeding in the African malaria mosquito (*Anopheles gambiae*). *Insect Mol Biol* 19: 683-693.
50. Zhu, F., Xu, J., Palli, R., Ferguson, J. and Palli, S. R. (2011) Ingested RNA interference for managing the populations of the Colorado potato beetle, *Leptinotarsa decemlineata*. Pest management science 67: 175-182.

What is claimed is:

1. A composition for controlling insects, comprising double-stranded RNA molecules, wherein said double-stranded RNA molecules encode the small or large ribosomal subunit, wherein said double stranded RNA molecules of said small ribosomal subunit are produced by transcription of nucleic acid sequences encoding a region of the insect ribosomal protein RPS 6, with the nucleotide sequence of SEQ ID NO: 230, and wherein said large ribosomal subunit are produced by transcription of nucleic acid sequences encoding a region of the insect ribosomal protein RPS 26, with the nucleotide sequence of SEQ ID NO: 231.

2. The composition of claim 1, wherein said composition comprises one or more double-stranded RNA molecules encoding mosquito ribosomal proteins, wherein said double-stranded RNA molecules are transcribed from nucleic acid sequences selected from the group consisting of SEQ ID Nos. 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 121, 124, 127, 130, 133, 136, 139, 142, 146, 149, 152, 155, 158, 161, 164, 167, 170, 173, 176, 179, 182, 185, 188, 191, 194, 197, 200, 203, 206, 209 and 212.

3. The composition of claim 1, wherein said double-stranded RNA is incorporated into insect bait.

4. The composition of claim 1, wherein said double-stranded RNA molecule is included in and expressed from a viral vector.

5. The composition of claim 4, wherein said viral vector is baculovirus vector system.

6. A method of controlling insect populations, comprising inhibiting RNA encoding ribosomal proteins by exposing insects to a formulation comprising the composition of claim 1.

7. The method of claim 6, wherein said formulation is incorporated in insect bait.

8. The method of claim 6, wherein said formulation comprises one or more double-stranded RNA, wherein said double-stranded RNA molecules are transcribed from the nucleic acid sequences selected from the group consisting of SEQ ID Nos. 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 121, 124, 127, 130, 133, 136, 139, 142, 146, 149, 152, 155, 158, 161, 164, 167, 170, 173, 176, 179, 182, 185, 188, 191, 194, 197, 200, 203, 206, 209, 212, 230, and 231.

9. The method of claim 6, wherein said composition is expressed from an insect vector.

10. The method of claim 9, wherein said insect vector is baculovirus expression system.

* * * * *